US006419925B1

(12) United States Patent
Knapp et al.

(10) Patent No.: US 6,419,925 B1
(45) Date of Patent: Jul. 16, 2002

(54) TOXOPLASMA GONDII ANTIGENS, THE PREPARATION THEREOF AND THE USE THEREOF

(75) Inventors: Stefan Knapp; Robert Ziegelmaier; Hans Küpper, all of Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/968,927

(22) Filed: Oct. 3, 2001

Related U.S. Application Data

(62) Division of application No. 09/461,240, filed on Dec. 16, 1999, now Pat. No. 6,326,008, which is a division of application No. 08/301,162, filed on Sep. 6, 1994, now Pat. No. 6,022,546, which is a continuation of application No. 08/167,128, filed on Dec. 16, 1993, now abandoned, which is a continuation of application No. 07/623,086, filed on Dec. 6, 1980, now abandoned.

(30) Foreign Application Priority Data

Dec. 8, 1989 (DE) .......................................... 39 40 598

(51) Int. Cl.[7] .............................................. A61K 39/395
(52) U.S. Cl. ................................ 424/151.1; 424/130.1; 424/141.1; 424/150.1; 530/387.1; 530/388.1; 530/388.2; 530/388.6
(58) Field of Search .......................... 424/130.1, 141.1, 424/150.1, 151.1; 530/387.1, 388.1, 388.2, 388.6

(56) References Cited

U.S. PATENT DOCUMENTS 5,429,922 A 7/1995 Sibley et al.

FOREIGN PATENT DOCUMENTS

| EP | A-301961 | 2/1989 |
| EP | 0 301 961 A1 | 2/1989 |
| WO | WO 89/05658 | 6/1989 |
| WO | WO 89/08700 | 9/1989 |

OTHER PUBLICATIONS

A. Johnson et al., Gene, vol. 85, pp. 215–220 (1989), Cloning Expression and Nucleotide Sequence of the Gene Fragment Encoding an Antigenic Portion of the Nucleoside Triphosphate Hydrolase of T. Gondii.

M.F. Cesbron–Delauw et al., Proc. Natl. Acad. Sci. USA, vol. 86, pp. 7537–7541 (1989), Molecular characterization of a 23–kilodalton major antigen secreted by Toxoplasma gondii.
J. Burg et al., J. Immunol., vol. 141, pp. 3584–3591 (1988), M olecular Analysis of the Gene Encoding the Major Surface Antigen of T. Gondii.
G. Koch et al. Characterization of Monoclonal Antibodies Against Tox oplasma Gondii, Zeitschrift fur die gesam te Hygiene und ihre G renzgebiete, pp. 615–617.
H.P.A. Hughes, Curr. Top. M icrobiol. (1985) 120:105–39.
E. Handman et al. Immunol. (1980) 40:570–88.
I. Potasman et al., J. Infect. Diseases (1986) 154:650–7.
A. Decoster et al., Clinic. Ex per. Immunol. (1988) 73:376–82.
H.A. Ehrlich, et al., Infect. Immun. (1983) 41:683–90.
S.D. Nagel and J.C. Boothroy d, J. Biol. Chem. (1989) 264:5569–76.
I. Potasman et al., J. clin. Microbiol. (1986) 24:1050–4.
J.B. Prince et al., Mol. Biochem. Parasitol. (1989) 34:3–14.
I. Braveny et al., Tropenmed. Parasit. (1978) 432–4.
P. Chomczynski and N. Sacci. Anal. Biochem. (1987) 162:156–9.
U. Gubler, Nucl. Acids Res. (1988) 16:2726.
L.S. Ozaki, et al., J. Immun. Method. (1986) 16:2726.
Promega Biotec.. ProtoBlot Im munoscreening Sy stem. (1986) Technical M anual.
R.A. Young and R.W. Davis. Proc. Natl. Acad. Sci. (1983) 80:1194–8.
R. Brent and N. Ptashne, Proc.Natl. Acad. Sci. (1981) 78:4202–8.
T.V. Huynh et al. in: Glover, DNA Cloning Volume e I (1985) pp. 49–78 IRL Press. O xford.
F. Sanger et al., Proc. Natl. Acad. Sci. (1977) 74:5463–7.
S. Knapp et al., Bio Techniques (1990) 8:280.
Johnson et al., Gene 85:215–20 (1989).
Kasper et al. Jour. of Immun. 132:443–449.
Johnson et al., Biochem. and Bophys. Res. Com. 100:934–43.
Kimata et al., Journal of Cell Science 88:231–239, 1987.

*Primary Examiner*—Jennifer E. Graser
(74) *Attorney, Agent, or Firm*—Finnegan, Henderson, Farabow, Garrett and Dunner, L.L.P.

(57) ABSTRACT

The present invention relates to the identification of *toxoplasma gondii* antigens and the preparation thereof by genetic engineering. A cDNA expression gene bank of this parasite was prepared. Recombinant clones which are of diagnostic interest were identified using a high-titer rabbit anti-*Toxoplasma gondii* serum, and isolated.

22 Claims, No Drawings

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 1179 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
CATATACTGC ACTGACTTCG ACACCATGGA GCAAAGGCTG CCAATTATTC TACTTGTTCT      60
CTCTGTGTTC TTCAGTTCAA CCCCAAGCGC CGCCCTTTCG AGCCACAATG GAGTCCCCGC     120
TTATCCATCG TATGCACAGG TATCGCTCTC TTCCAACGGC GAGCCACGGC ACAGGGGCAT     180
ACGCGGCAGC TTCCTCATGT CCGTAAAGCC ACACGCAAAC GCTGATGACT TCGCCTCCGA     240
CGACAACTAC GAACCGCTGC CGAGTTTCGT GGAAGCTCCT GTCAGAGGCC CGGACCAAGT     300
CCCTGCCAGA GGAGAAGCTG CTCTTGTCAC AGAGGAGACT CCAGCGCAAC AGCCGGCGGT     360
GGCTCTAGGC AGTGCAGAAG GGGAGGGGAC TCCACCTACT GAATCCGCCT CCGAAAAATTC    420
TGAAGATGAT GACACGTTTC ACGATGCCCT CCAAGAGCTT CCAGAGGATG GCCTCGAAGT     480
GCGCCCACCA AATGCACAGG AGCTGCCCCC ACCAAATGTA CAGGAGCTGC CCCCACCAAA     540
TGTACAGGAG CTGCCCCCAC CAACTGAACA GGAGCTGCCC CCACCAACTG AACAGGAGCT     600
GCCCCCACCA ACTGAACAGG AGCTGCCCCC ACCAACTGAA CAGGAGCTAG CCCCATCAAC     660
TGAACAGGAG CTGCCCCCAC CAGTGGGCGA AGGTCAACGT CTGCAAGTCC CTGGGGAACA     720
TGGGCCACAG GGGCCCCCAT ACGATGATCA GCAGCTGCTT TTAGAGCCTA CGGAAGAGCA     780
ACAGGAGGGC CCTCAGGAGC CGCTGCCACC GCCGCCGCCC CCGACTCGGG GCGAACAACC     840
CGAAGGACAG CAGCCGCAGG GACCAGTTCG TCAAAATTTT TTTCGTCGGG CGTTGGGGGC     900
CGCAAGAAGC CGATTCGGAG GTGCACGACG CCATGTCAGT GGGGTGTTCC GAAGAGTCAG     960
AGGTGGTTTG AACCGTATAG TAGGTGGAGT GAGGAGTGGT TCAGGCGTG CAAGAGAAGG     1020
```

-continued

```
TGTCGTTGGG GGAGTCCGTC GTTTAACAAG TGGTGCCAGT CTGGGTCTCG GTCGTGTAGG    1080

AGAAGGTTTA GGTAGGAGTT TCTATCGTGT AAGAGGAGCT GTCAGTAGCG GTCGTAGGCG    1140

TGCAGCAGAT GGTGCCAGCA ATGTAAGAGA AAGATTCGT                           1179
```

(2) INFORMATION FOR SEQ ID NO: 2:

(i) SEQUENCE CHARACTERISTICS:
       (A) LENGTH: 392 amino acids
       (B) TYPE: amino acid
       (D) TOPOLOGY: linear (ii) MOLECULE TYPE: peptide (xi) SEQUENCE DESCRIPTION: SEQ ID NO: 2:

```
Ile Tyr Cys Thr Asp Phe Asp Thr Met Glu Gln Arg Leu Pro Ile Ile
 1               5                  10                  15

Leu Leu Val Leu Ser Val Phe Phe Ser Ser Thr Pro Ser Ala Ala Leu
            20                  25                  30

Ser Ser His Asn Gly Val Pro Ala Tyr Pro Ser Tyr Ala Gln Val Ser
        35                  40                  45

Leu Ser Ser Asn Gly Glu Pro Arg His Arg Gly Ile Arg Gly Ser Phe
 50                  55                  60

Leu Met Ser Val Lys Pro His Ala Asn Ala Asp Asp Phe Ala Ser Asp
65                  70                  75                  80

Asp Asn Tyr Glu Pro Leu Pro Ser Phe Val Glu Ala Pro Val Arg Gly
                85                  90                  95

Pro Asp Gln Val Pro Ala Arg Gly Glu Ala Ala Leu Val Thr Glu Glu
            100                 105                 110

Thr Pro Ala Gln Gln Pro Ala Val Ala Leu Gly Ser Ala Glu Gly Glu
        115                 120                 125

Gly Thr Pro Pro Thr Glu Ser Ala Ser Glu Asn Ser Glu Asp Asp Asp
    130                 135                 140

Thr Phe His Asp Ala Leu Gln Glu Leu Pro Glu Asp Gly Leu Glu Val
145                 150                 155                 160

Arg Pro Pro Asn Ala Gln Glu Leu Pro Pro Asn Val Gln Glu Leu
                165                 170                 175

Pro Pro Pro Asn Val Gln Glu Leu Pro Pro Thr Glu Gln Glu Leu
            180                 185                 190

Pro Pro Pro Thr Glu Gln Glu Leu Pro Pro Thr Glu Gln Glu Leu
        195                 200                 205

Pro Pro Pro Thr Glu Gln Glu Leu Ala Pro Ser Thr Glu Gln Glu Leu
    210                 215                 220

Pro Pro Pro Val Gly Glu Gly Gln Arg Leu Gln Val Pro Gly Glu His
225                 230                 235                 240

Gly Pro Gln Gly Pro Tyr Asp Asp Gln Gln Leu Leu Glu Pro
                245                 250                 255

Thr Glu Gln Gln Glu Gly Pro Gln Glu Pro Leu Pro Pro Pro
            260                 265                 270

Pro Pro Thr Arg Gly Glu Gln Pro Glu Gly Gln Gln Pro Gln Gly Pro
        275                 280                 285

Val Arg Gln Asn Phe Phe Arg Arg Ala Leu Gly Ala Ala Arg Ser Arg
    290                 295                 300

Phe Gly Gly Ala Arg Arg His Val Ser Gly Val Phe Arg Arg Val Arg
305                 310                 315                 320

Gly Gly Leu Asn Arg Ile Val Gly Gly Val Arg Ser Gly Phe Arg Arg
```

```
            325                 330                 335
Ala Arg Glu Gly Val Val Gly Val Arg Arg Leu Thr Ser Gly Ala
                340                 345                 350

Ser Leu Gly Leu Gly Arg Val Gly Glu Gly Leu Gly Arg Ser Phe Tyr
            355                 360                 365

Arg Val Arg Gly Ala Val Ser Ser Gly Arg Arg Ala Ala Asp Gly
        370                 375                 380

Ala Ser Asn Val Arg Glu Arg Phe
385                 390

(2) INFORMATION FOR SEQ ID NO: 3:

(i) SEQUENCE CHARACTERISTICS:
        (A) LENGTH: 921 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CTGAACAGGA GGGTTTGCCG GAAACAGAGG TGGCGCATCA GCATGAGACA GAAGAACAGT      60
ACGGGACTGA AGGGATGCCC CCCCCTGTTC TGCCACCTGC ACCGGTAGTC CATCCGCGTT     120
TTATTGCAGT ACCAGGGCCG TCGGTGCCTG TTCCATTTTT CAGTTTGCCA GACATCCACC     180
CGGATCAGGT TGTGTATATT CTAAGGGTTC AGGGATCTGG GGACTTCGAC ATCAGTTTCG     240
AAGTTGGCCG AGCTGTGAAG CAGTTGGAAG CCATCAAGAA AGCATACAGA GAAGCCACCG     300
GGAAGCTAGA AGCAGACGAG CTTGAGTCAG AAAGGGGACC TGCTGTTTCA CCTCGACGAA     360
GGCTGGTTGA CCTGATCAAA GATAACCAGC GACGACTCAG GGCGGCGCTT CAGAAGATAA     420
AGATACAGAA AAAGTTGGAG GAGATTGATG ACTTACTTCA GCTGACACGC GCACTGAAGG     480
CCATGGATGC CCGTCTGAGA GCCTGCCAGG ATATGGCACC GATTGAGGAG GCGCTGTGTC     540
ACAAGACGAA GGCGTTTGGA GAAATGGTGT CCCAGAAAGC CAAGGAAATT CGGGAGAAAG     600
CGGCGTCCTT GTCTTCATTG TTAGGTGTCG ATGCTGTCGA AAAAGAATTG CGGCGTGTCG     660
AACCGGAACA TGAAGATAAC ACCAGAGTTG AAGCCAGGGT AGAGGAATTG CAGAAGGCGC     720
TGGAGAAGGC CGCGTCTGAG GCAAAGCAGC TCGTGGGGAC CGCAGCAGGC GAAATAGAGG     780
AAGGAGTAAA AGCGGATACT CAGGCTGTGC AAGATAGCTC GAAAGACGTG TTGACGAAGA     840
GTCCAGTTGC GCTCGTGGAA GCCTTTAAAG CGATCCAGAG GGCTCTTCTT GAGGCGAAGA     900
CAAAGGAACT AGTAGAGCCT A                                               921

(2) INFORMATION FOR SEQ ID NO: 4:

(i) SEQUENCE CHARACTERISTICS:
        (A) LENGTH: 306 amino acids
        (B) TYPE: amino acid
        (D) TOPOLOGY: linear (ii) MOLECULE TYPE: peptide (xi) SEQUENCE DESCRIPTION: SEQ ID NO: 4:

Glu Gln Glu Gly Leu Pro Glu Thr Glu Val Ala His Gln His Glu Thr
1               5                   10                  15

Glu Glu Gln Tyr Gly Thr Glu Gly Met Pro Pro Pro Val Leu Pro Pro
            20                  25                  30

Ala Pro Val Val His Pro Arg Phe Ile Ala Val Pro Gly Pro Ser Val
        35                  40                  45
```

```
Pro Val Pro Phe Phe Ser Leu Pro Asp Ile His Pro Asp Gln Val Val
    50                  55                  60
Tyr Ile Leu Arg Val Gln Gly Ser Gly Asp Phe Asp Ile Ser Phe Glu
65                  70                  75                  80
Val Gly Arg Ala Val Lys Gln Leu Glu Ala Ile Lys Lys Ala Tyr Arg
                85                  90                  95
Glu Ala Thr Gly Lys Leu Glu Ala Asp Glu Leu Glu Ser Glu Arg Gly
                100                 105                 110
Pro Ala Val Ser Pro Arg Arg Arg Leu Val Asp Leu Ile Lys Asp Asn
                115                 120                 125
Gln Arg Arg Leu Arg Ala Ala Leu Gln Lys Ile Lys Ile Gln Lys Lys
130                 135                 140
Leu Glu Glu Ile Asp Asp Leu Leu Gln Leu Thr Arg Ala Leu Lys Ala
145                 150                 155                 160
Met Asp Ala Arg Leu Arg Ala Cys Gln Asp Met Ala Pro Ile Glu Glu
                165                 170                 175
Ala Leu Cys His Lys Thr Lys Ala Phe Gly Glu Met Val Ser Gln Lys
                180                 185                 190
Ala Lys Glu Ile Arg Glu Lys Ala Ala Ser Leu Ser Ser Leu Leu Gly
                195                 200                 205
Val Asp Ala Val Glu Lys Glu Leu Arg Arg Val Glu Pro Glu His Glu
                210                 215                 220
Asp Asn Thr Arg Val Glu Ala Arg Val Glu Glu Leu Gln Lys Ala Leu
225                 230                 235                 240
Glu Lys Ala Ala Ser Glu Ala Lys Gln Leu Val Gly Thr Ala Ala Gly
                245                 250                 255
Glu Ile Glu Glu Gly Val Lys Ala Asp Thr Gln Ala Val Gln Asp Ser
                260                 265                 270
Ser Lys Asp Val Leu Thr Lys Ser Pro Val Ala Leu Val Glu Ala Phe
                275                 280                 285
Lys Ala Ile Gln Arg Ala Leu Leu Glu Ala Lys Thr Lys Glu Leu Val
290                 295                 300
Glu Pro
305

(2) INFORMATION FOR SEQ ID NO: 5:

(i) SEQUENCE CHARACTERISTICS:
        (A) LENGTH: 226 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GCCGGAACTA ACAGAGGAGC AACAGAGAGG CGACGAACCC CTAACCACCG GCCAGAATGT      60

GGGCACTGTG TTAGGCTTCG CAGCGCTTGC TGCTGCCGCA GCGTTCCTTG GCATGGGTCT     120

CACGAGGACG TACCGACATT TTTCCCCACG CAAAAACAGA TCACGGCAGC CTGCACTCGA     180

GCAAGAGGTG CCTGAATCAG GCGAAGATGG GGAGGATGCC CGCCAG                   226

(2) INFORMATION FOR SEQ ID NO: 6:

(i) SEQUENCE CHARACTERISTICS:
        (A) LENGTH: 75 amino acids
        (B) TYPE: amino acid
```

(D) TOPOLOGY: linear (ii) MOLECULE TYPE: peptide (xi) SEQUENCE DESCRIPTION: SEQ ID NO: 6:

```
Pro Glu Leu Thr Glu Glu Gln Arg Gly Asp Glu Pro Leu Thr Thr
1               5                  10                  15

Gly Gln Asn Val Gly Thr Val Leu Gly Phe Ala Ala Leu Ala Ala Ala
            20                  25                  30

Ala Ala Phe Leu Gly Met Gly Leu Thr Arg Thr Tyr Arg His Phe Ser
            35                  40                  45

Pro Arg Lys Asn Arg Ser Arg Gln Pro Ala Leu Glu Gln Glu Val Pro
50                  55                  60

Glu Ser Gly Glu Asp Gly Glu Asp Ala Arg Gln
65                  70                  75
```

(2) INFORMATION FOR SEQ ID NO: 7:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
CCGTTGCTGT CGGGGTGCTA TCTTCTCCCA CCTTTTATCA GTTAAGTTGT ACAGTGAGTG      60

TCAGCTTGTT TCGACACGTC TGTATAGACG CAACTCGGTT TGCTTGTGTT GTTTGGTGGC     120

TGGCCAAATC AAAGGCTATT CATTTTTCAC TTGCTGTTGT TCTTTGAAGA AATCAAGCAA     180

GATGGTGCGT GTGAGCGCTA TTGTCGGAGC TGCTGCATCG GTGTTCGTGT GCCTGTCTGC     240

CGGCGCTTAC GCTGCCGAAG GCGGCGACAA CCAGTCGAGC GCCGTCTCAG ATCGGGCGTC     300

TCTCTTTGGT TTGCTGAGTG GAGGGACAGG GCA                                  333
```

(2) INFORMATION FOR SEQ ID NO: 8:

(i) SEQUENCE CHARACTERISTICS:
        (A) LENGTH: 110 amino acids
        (B) TYPE: amino acid
        (D) TOPOLOGY: linear (ii) MOLECULE TYPE: peptide (xi) SEQUENCE DESCRIPTION: SEQ ID NO: 8:

```
Arg Cys Cys Arg Gly Ala Ile Phe Ser His Leu Leu Ser Val Lys Leu
1               5                  10                  15

Tyr Ser Glu Cys Gln Leu Val Ser Thr Arg Leu Tyr Arg Arg Asn Ser
            20                  25                  30

Val Cys Leu Cys Cys Leu Val Ala Gly Gln Ile Lys Gly Tyr Ser Phe
            35                  40                  45

Phe Thr Cys Cys Cys Ser Leu Lys Ser Ser Lys Met Val Arg Val
            50                  55                  60

Ser Ala Ile Val Gly Ala Ala Ser Val Phe Val Cys Leu Ser Ala
65                  70                  75                  80

Gly Ala Tyr Ala Ala Glu Gly Gly Asp Asn Gln Ser Ser Ala Val Ser
                85                  90                  95

Asp Arg Ala Ser Leu Phe Gly Leu Leu Ser Gly Gly Thr Gly
                100                 105                 110
```

(2) INFORMATION FOR SEQ ID NO: 9:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
CAGTTTCGCG CGTCCCGTTT CCACGGACAA AATGGCAATG AAATACGTCG CTGCTTACCT      60

GATGGTGGTG CTGTCGGGAA CCGACACTCC GACCAAGAAG CAGGTTGAGA AAACCCTCTC     120

CTCTGTGGGT ATTGATGTTG AAGACGACAT CATGGACACC TTCTTCAAAG CTGTCGAAGG     180

AAAGACCCCC CACGAGCTGA TTGCCGCGGG TATGGAGAAG CTCCAGAAGG TACCTTCTGG     240

TGGTGTCGCT GCTGCTGCTG CTCCTGCTGC TGGCGCTGCC GATGCTGGTG CGGGTGCTGC     300

TGCTGCGAAG AAGGAGGAGG AAAAGAAGGA GGAAGAGGAG GAGGAAGACG ACATG          355
```

(2) INFORMATION FOR SEQ ID NO: 10:

(i) SEQUENCE CHARACTERISTICS:
        (A) LENGTH: 118 amino acids
        (B) TYPE: amino acid
        (D) TOPOLOGY: linear (ii) MOLECULE TYPE: peptide (xi) SEQUENCE DESCRIPTION: SEQ ID NO: 10:

```
Ser Phe Ala Arg Pro Val Ser Thr Asp Lys Met Ala Met Lys Tyr Val
 1               5                  10                  15

Ala Ala Tyr Leu Met Val Val Leu Ser Gly Thr Asp Thr Pro Thr Lys
                20                  25                  30

Lys Gln Val Glu Lys Thr Leu Ser Ser Val Gly Ile Asp Val Glu Asp
            35                  40                  45

Asp Ile Met Asp Thr Phe Phe Lys Ala Val Glu Gly Lys Thr Pro His
        50                  55                  60

Glu Leu Ile Ala Ala Gly Met Glu Lys Leu Gln Lys Val Pro Ser Gly
65                  70                  75                  80

Gly Val Ala Ala Ala Ala Pro Ala Ala Gly Ala Ala Asp Ala Gly
                85                  90                  95

Ala Gly Ala Ala Ala Ala Lys Lys Glu Glu Glu Lys Lys Glu Glu Glu
                100                 105                 110

Glu Glu Glu Asp Asp Met
            115
```

(2) INFORMATION FOR SEQ ID NO: 11:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
GCCACAGCCA GAGATACCGC CTGTTCATCG GCCGCCGCCT CCGGGTTTCC GTCCCGAAGT      60

GGCTCCCGTG CCCCCGTATC CAGTGGGCAC TCCAACGGGC ATGCCCCAGC CGGAGATACC     120

GGCAGTTCAC CATCCGTTCC CCTACGTTAC GACAACCACG ACAG                     164
```

(2) INFORMATION FOR SEQ ID NO: 12:

(i) SEQUENCE CHARACTERISTICS:
        (A) LENGTH: 54 amino acids
        (B) TYPE: amino acid
        (D) TOPOLOGY: linear (ii) MOLECULE TYPE: peptide (xi) SEQUENCE DESCRIPTION: SEQ ID NO: 12:

```
Pro Gln Pro Glu Ile Pro Pro Val His Arg Pro Pro Pro Gly Phe
1               5                   10                  15

Arg Pro Glu Val Ala Pro Val Pro Tyr Pro Val Gly Thr Pro Thr
            20                  25                  30

Gly Met Pro Gln Pro Glu Ile Pro Ala Val His His Pro Phe Pro Tyr
        35                  40                  45

Val Thr Thr Thr Thr Thr
        50
```

(2) INFORMATION FOR SEQ ID NO: 13:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
ATATATGTGT CTCGTGCTTG AGTGTGTTCT TTGTATGATC AAAACTCGTT AAAATGCGCA     60

CGTTACCGCA TGGGTAGTAG TTCGAGACAG CTTGTGTGTA CCTGAGGGGC CGCGTGTTGC    120

CAAAAGTGCC TAGTCTTACA CGGCCGACAA GAGGGTTCCT CGGTTCTTCT CTGCGTTCTT    180

CCTTCTCCCA TCCGATTCTT CAAGTTCTGA ACAAATCTGT CGTGTCTCGA CTGATGTGCG    240

TGCGTTTTGA                                                           250
```

(2) INFORMATION FOR SEQ ID NO: 14:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
GGAATTCTTG TTACGCGGTC AGATGTTTCT TGAGTAGTGA ATCAAAATGT ATTATGGTGT     60

AATCCTGTCA GTTTTATACG TATTGTCATA CGTCCACGCA TCTCACGTAC GGGCGCGAAC    120

GCAGCAAGTG ACGAGAGATC ATCCCACTCG TTTGGTGACG CTGCAAAATA CAAGTGTATT    180

ATACGGTCAG TCGGCTCTAC AACATTCAAA ACGAGTTGTC TCGCTTCAAC CACAAAGCGC    240

CACACT                                                               246
```

(2) INFORMATION FOR SEQ ID NO: 15:

(i) SEQUENCE CHARACTERISTICS:
        (A) LENGTH: 1092 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
CAGTTTCCGC GCTGTAGTAA GATGGCTTTA CCATTGCGTG TTTCGGCCAC GGTGTTCGTG      60
GTCTTCGCTG TCTTTGGTGT AGCTCGCGCC ATGAACGGTC CTTTGAGTTA TCATCCAAGC     120
AGTTACGGAG CGTCGTATCC GAATCCGAGT AATCCTCTGC ATGGAATGCC CAAGCCAGAG     180
AACCCGGTGA GACCGCCTCC TCCCGGTTTC CATCCAAGCG TTATTCCCAA TCCCCCGTAC     240
CCGCTGGGCA CTCCAGCGAG CATGCCACAG CCAGAGGTTC CGCCACTTCA GCATCCCCCG     300
CCAACGGGTT CCCCTCCCGC GGCCGCTCCC CAGCCTCCAT ATCCAGTGGG TACTCCAGTA     360
ATGCCACAGC CAGAGATACC GCCTGTTCAT CGGCCGCCGC CTCCGGGTTT CCGTCCCGAA     420
GTGGCTCCCG TGCCCCCGTA TCCAGTGGGC ACTCCAACGG GCATGCCCCA GCCGGAGATA     480
CCGGCAGTTC ACCATCCGTT CCCCTACGTT ACGACAACCA CGACAGCTGC TCCTCGTGTG     540
CTGGTTTATA AGATTCCCTA TGGAGGCGCT GCACCCCCCC GTGCTCCTCC AGTGCCACCC     600
CGTATGGGCC CGAGTGATAT CAGCACTCAC GTGCGGGGTG CAATCCGGCG TCAACCCGGT     660
ACCACCACCA CCACTACTTC CCGCAAACTA CTATTCAGGA CAGCGGTAGT GGCTGCAATG     720
GCAGCAGCCT TGATAACCCT GTTCAGACAA AGACCTGTGT TCATGGAGGG GGTACGGATG     780
TTTCCAAATC TCCACTACAG ATTCACCGTA ACGACGCAGA ATTAAATTTC CGGTTGACGA     840
ATATAGAAGT CACTTATACA GTGGGTACAC GACCTTCGTG GCGTCCACAC CTTGTTTCCG     900
TTCCGGTCAC AGGTTGTGTC TACAAACGAA CACGGTGGTA TGTGCTGTAG ACTCAGGGGT     960
GGGAGGAGCG CTGTAGGGCC TTCTGGAGAG CTCTCAATGT GCGCTATCCG CTTATATTCG    1020
TGCAGCGTTA TCCTCGTGAG GAGCGTCGAT TGTGTCGTGC CCAGTCTCGC CGGACTCGAA    1080
TCAGAAACCT GC                                                        1092
```

(2) INFORMATION FOR SEQ ID NO: 16:

(i) SEQUENCE CHARACTERISTICS:
      (A) LENGTH: 267 amino acids
      (B) TYPE: amino acid
      (D) TOPOLOGY: linear (ii) MOLECULE TYPE: peptide (xi) SEQUENCE DESCRIPTION: SEQ ID NO: 16:

```
Met Ala Leu Pro Leu Arg Val Ser Ala Thr Val Phe Val Val Phe Ala
1               5                   10                  15

Val Phe Gly Val Ala Arg Ala Met Asn Gly Pro Leu Ser Tyr His Pro
            20                  25                  30

Ser Ser Tyr Gly Ala Ser Tyr Pro Asn Pro Ser Asn Pro Leu His Gly
        35                  40                  45

Met Pro Lys Pro Glu Asn Pro Val Arg Pro Pro Pro Gly Phe His
    50                  55                  60

Pro Ser Val Ile Pro Asn Pro Tyr Pro Leu Gly Thr Pro Ala Ser
65                  70                  75                  80

Met Pro Gln Pro Glu Val Pro Pro Leu Gln His Pro Pro Thr Gly
            85                  90                  95

Ser Pro Pro Ala Ala Ala Pro Gln Pro Pro Tyr Pro Val Gly Thr Pro
            100                 105                 110

Val Met Pro Gln Pro Glu Ile Pro Pro Val His Arg Pro Pro Pro Pro
            115                 120                 125
```

```
Gly Phe Arg Pro Glu Val Ala Pro Val Pro Pro Tyr Pro Val Gly Thr
    130                 135                 140
Pro Thr Gly Met Pro Gln Pro Glu Ile Pro Ala Val His His Pro Phe
145                 150                 155                 160
Pro Tyr Val Thr Thr Thr Thr Ala Ala Pro Arg Val Leu Val Tyr
                165                 170                 175
Lys Ile Pro Tyr Gly Gly Ala Ala Pro Pro Arg Ala Pro Pro Val Pro
            180                 185                 190
Pro Arg Met Gly Pro Ser Asp Ile Ser Thr His Val Arg Gly Ala Ile
            195                 200                 205
Arg Arg Gln Pro Gly Thr Thr Thr Thr Thr Ser Arg Lys Leu Leu
    210                 215                 220
Phe Arg Thr Ala Val Val Ala Ala Met Ala Ala Ala Leu Ile Thr Leu
225                 230                 235                 240
Phe Arg Gln Arg Pro Val Phe Met Glu Gly Val Arg Met Phe Pro Asn
                245                 250                 255
Leu His Tyr Arg Phe Thr Val Thr Thr Gln Asn
            260                 265
```

(2) INFORMATION FOR SEQ ID NO: 17:

(i) SEQUENCE CHARACTERISTICS:
        (A) LENGTH: 2074 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
TTGCTGTCGC CGTTGCTGTC GCATATACTG CACTGACTTC GACACCATGG AGCAAAGGCT    60
GCCAATTATT CTACTTGTTC TCTCTGTGTT CTTCAGTTCA ACCCCAAGCG CCGCCCTTTC   120
GAGCCACAAT GGAGTCCCCG CTTATCCATC GTATGCACAG GTATCGCTCT CTTCCAACGG   180
CGAGCCACGG CACAGGGGCA TACGCGGCAG CTTCCTCATG TCCGTAAAGC CACACGCAAA   240
CGCTGATGAC TTCGCCTCCG ACGACAACTA CGAACCGCTG CCGAGTTTCG TGGAAGCTCC   300
TGTCAGAGGC CCGGACCAAG TCCCTGCCAG AGGAGAAGCT GCTCTTGTCA CAGAGGAGAC   360
TCCAGCGCAA CAGCCGGCGG TGGCTCTAGG CAGTGCAGAA GGGGAGGGGA CTCCACCTAC   420
TGAATCCGCC TCCGAAAATT CTGAAGATGA TGACACGTTT CACGATGCCC TCCAAGAGCT   480
TCCAGAGGAT GGCCTCGAAG TGCGCCCACC AAATGCACAG GAGCTGCCCC CACCAAATGT   540
ACAGGAGCTG CCCCCACCAA ATGTACAGGA GCTGCCCCCA CCAACTGAAC AGGAGCTGCC   600
CCCACCAACT GAACAGGAGC TGCCCCCACC AACTGAACAG GAGCTGCCCC CACCAACTGA   660
ACAGGAGCTA GCCCCATCAA CTGAACAGGA GCTGCCCCCA CCAGTGGGCG AAGGTCAACG   720
TCTGCAAGTC CCTGGGGAAC ATGGGCCACA GGGGCCCCCA TACGATGATC AGCAGCTGCT   780
TTTAGAGCCT ACGAAGAGC AACAGGAGGG CCCTCAGGAG CCGCTGCCAC CGCCGCCGCC   840
CCCGACTCGG GGCGAACAAC CCGAAGGACA GCAGCCGCAG GGACCAGTTC GTCAAAATTT   900
TTTTCGTCGG GCGTTGGGGG CCGCAAGAAG CCGATTCGGA GGTGCACGAC GCCATGTCAG   960
TGGGGTGTTC CGAAGAGTCA GAGGTGGTTT GAACCGTATA GTAGGTGGAG TGAGGAGTGG  1020
TTTCAGGCGT GCAAGAGAAG GTGTCGTTGG GGGAGTCCGT CGTTTAACAA GTGGTGCCAG  1080
TCTGGGTCTC GGTCGTGTAG GAGAAGGTTT AGGTAGGAGT TTCTATCGTG TAAGAGGAGC  1140
TGTCAGTAGC GGTCGTAGGC GTGCAGCAGA TGGTGCCAGC AATGTAAGAG AAAGATTCGT  1200
```

```
TGCCGCAGGC GGGAGAGTCA GAGACGCTTT CGGCGCGGGA TTGACGCGCC TCCGCAGGCG    1260

CGGCAGAACT AATGGCGAGG AGGGCAGGCC CCTACTGGGC GAAGGAAGAG AGCAGGATGA    1320

TGGATCGCAA TAATACGGGC AGCATGCTGC TGGATTCGGC GAAGACGACC GTTTCTCGTA    1380

AACGACAGCG GGTCCTCCGA AGTTAAGAAA CCCGGTAAAC GTGTGTGCCG TAACGGTGAT    1440

CGAGTTTGCA GATGGTTCCT TGTGTACCAC GTGGCTTCTC GAGACCAATC GTGCTTTGTT    1500

AGGGTCTAGT AGTTCGGACA GGATTTTATT GAACTGCAGG AATGCTTGCA GAAGAGAAGC    1560

CGTGAGGCAA TGCAGGTTCT TGCGTCTGTG CGAGCAGGAC TTGAAAGATT CGTTGTGGTG    1620

GCAACCTTGT GCCTATCTAT CCGAAGCCTC GCTGACTCGC AGAAATAAGG GTCGAGATCC    1680

ATGAGAGCTT TCTGGGTGGT GAGGCCAGGG CTTGTGAGAA CTTCGTGGGA AGATGTGCTT    1740

GAGCTTCGTC AGCAACTTCA CGGAGAGCGC CACCTGATCT AAACATCCGA ACATTTTTAG    1800

CTCGACATGT TCACAGAAAT GTTGATAGGT TGAGGCGTGT AAAGGTTCGT TCTGGGAAGA    1860

CGAGTAATCA TGTCACGCCA TGTTAGCGGT CATGTCGCTG CCTCATTGTA TTCGGGTGTC    1920

ACTGTGCCTT CAAACATCAG TCGTGGTTCA GCAGTGTTTG CTGACGTTCG ACACACGGAA    1980

CTCCGGCGAG ACTGTCTCGG CAAATGTGAC GCACTTTGTA TTCATGTGGC AAACCGTTTC    2040

AACGCGGTAA TGTGTTTTCT TGTTAAAAAA AAAA                                2074
```

(2) INFORMATION FOR SEQ ID NO: 18:

(i) SEQUENCE CHARACTERISTICS:
        (A) LENGTH: 428 amino acids
        (B) TYPE: amino acid
        (D) TOPOLOGY: linear (ii) MOLECULE TYPE: peptide (xi) SEQUENCE DESCRIPTION: SEQ ID NO: 18:

```
Met Glu Gln Arg Leu Pro Ile Ile Leu Leu Val Leu Ser Val Phe Phe
 1               5                  10                  15

Ser Ser Thr Pro Ser Ala Ala Leu Ser Ser His Asn Gly Val Pro Ala
                20                  25                  30

Tyr Pro Ser Tyr Ala Gln Val Ser Leu Ser Ser Asn Gly Glu Pro Arg
            35                  40                  45

His Arg Gly Ile Arg Gly Ser Phe Leu Met Ser Val Lys Pro His Ala
 50                  55                  60

Asn Ala Asp Asp Phe Ala Ser Asp Asp Asn Tyr Glu Pro Leu Pro Ser
 65                  70                  75                  80

Phe Val Glu Ala Pro Val Arg Gly Pro Asp Gln Val Pro Ala Arg Gly
                85                  90                  95

Glu Ala Ala Leu Val Thr Glu Glu Thr Pro Ala Gln Gln Pro Ala Val
            100                 105                 110

Ala Leu Gly Ser Ala Glu Gly Glu Gly Thr Pro Pro Thr Glu Ser Ala
            115                 120                 125

Ser Glu Asn Ser Glu Asp Asp Asp Thr Phe His Asp Ala Leu Gln Glu
            130                 135                 140

Leu Pro Glu Asp Gly Leu Glu Val Arg Pro Pro Asn Ala Gln Glu Leu
145                 150                 155                 160

Pro Pro Pro Asn Val Gln Glu Leu Pro Pro Asn Val Gln Glu Leu
                165                 170                 175

Pro Pro Pro Thr Glu Gln Glu Leu Pro Pro Pro Thr Glu Gln Glu Leu
            180                 185                 190
```

```
Pro Pro Pro Thr Glu Gln Glu Leu Pro Pro Pro Thr Glu Gln Glu Leu
            195                 200                 205

Ala Pro Ser Thr Glu Gln Glu Leu Pro Pro Pro Val Gly Glu Gly Gln
            210                 215                 220

Arg Leu Gln Val Pro Gly Glu His Gly Pro Gln Gly Pro Pro Tyr Asp
225                 230                 235                 240

Asp Gln Gln Leu Leu Glu Pro Thr Glu Gln Gln Glu Gly Pro
            245                 250                 255

Gln Glu Pro Leu Pro Pro Pro Pro Thr Arg Gly Glu Gln Pro
            260                 265                 270

Glu Gly Gln Gln Pro Gln Gly Pro Val Arg Gln Asn Phe Arg Arg
            275                 280                 285

Ala Leu Gly Ala Ala Arg Ser Arg Phe Gly Gly Ala Arg Arg His Val
            290                 295                 300

Ser Gly Val Phe Arg Arg Val Arg Gly Gly Leu Asn Arg Ile Val Gly
305                 310                 315                 320

Gly Val Arg Ser Gly Phe Arg Arg Ala Arg Glu Gly Val Val Gly Gly
                325                 330                 335

Val Arg Arg Leu Thr Ser Gly Ala Ser Leu Gly Leu Gly Arg Val Gly
            340                 345                 350

Glu Gly Leu Gly Arg Ser Phe Tyr Arg Val Arg Gly Ala Val Ser Ser
            355                 360                 365

Gly Arg Arg Arg Ala Ala Asp Gly Ala Ser Asn Val Arg Glu Arg Phe
370                 375                 380

Val Ala Ala Gly Gly Arg Val Arg Asp Ala Phe Gly Ala Gly Leu Thr
385                 390                 395                 400

Arg Leu Arg Arg Arg Gly Arg Thr Asn Gly Glu Gly Arg Pro Leu
            405                 410                 415

Leu Gly Glu Gly Arg Glu Gln Asp Asp Gly Ser Gln
            420                 425

(2) INFORMATION FOR SEQ ID NO: 19:

(i) SEQUENCE CHARACTERISTICS:
        (A) LENGTH: 1909 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GCCACTGCTG TGTCTGAAGC GTGCCGATGT GTGCGCGTAC GCTTACAGAG AGCCTGCAAG      60

ACACTGGTTG GAAGACAAAA TTTTTCTTCT CAAGAGTTGA GCTTTAGTTT GGTCACTCGC     120

CGTTGGTTGT TCTGTGTGCT AGACGTACTC TAACGCAAAC CAGTCGAGGA ACACACGAAC     180

GAGAGAGACG GCAATATCTC CCGTCGCGCT ATCATACCGG CAACATGGAT TGCGGACAGT     240

GCAGAAGGCA ACTGCACGCA GCAGGTGTTC TAGGCTTGTT TGTCACCCTT GCCACAGCAA     300

CCGTAGGATT GAGCCAAAGG GTGCCAGAGC TACCAGAAGT GGAGTCCTTT GATGAAGTAG     360

GCACGGGAGC TCGACGGTCC GGGTCCATTG CGACCCTTCT TCCACAAGAC GCTGTTTTAT     420

ATGAGAACTC AGAGGACGTT GCCGTTCCGA GTGATTCAGC ATCGACCCCG TCATACTTTC     480

ATGTGGAATC TCCAAGTGCT AGTGTGGAAG CCGCGACTGG CGCGGTGGGA GAGGTGGTGC     540

CGGACTGTGA AGAACGACAG GAACAGGGTG ACACGACGTT ATCCGATCAC GATTTCCATT     600

CAGGTGGAAC TGAACAGGAG GGTTTGCCGG AAACAGAGGT GGCGCATCAG CATGAGACAG     660
```

```
AAGAACAGTA CGGGACTGAA GGGATGCCCC CCCCTGTTCT GCCACCTGCA CCGGTAGTCC    720

ATCCGCGTTT TATTGCAGTA CCAGGGCCGT CGGTGCCTGT TCCATTTTTC AGTTTGCCAG    780

ACATCCACCC GGATCAGGTT GTGTATATTC TAAGGGTTCA GGGATCTGGG GACTTCGACA    840

TCAGTTTCGA AGTTGGCCGA GCTGTGAAGC AGTTGGAAGC CATCAAGAAA GCATACAGAG    900

AAGCCACCGG GAAGCTAGAA GCAGACGAGC TTGAGTCAGA AAGGGGACCT GCTGTTTCAC    960

CTCGACGAAG GCTGGTTGAC CTGATCAAAG ATAACCAGCG ACGACTCAGG GCGGCGCTTC   1020

AGAAGATAAA GATACAGAAA AAGTTGGAGG AGATTGATGA CTTACTTCAG CTGACACGCG   1080

CACTGAAGGC CATGGATGCC CGTCTGAGAG CCTGCCAGGA TATGGCACCG ATTGAGGAGG   1140

CGCTGTGTCA CAAGACGAAG GCGTTTGGAG AAATGGTGTC CCAGAAAGCC AAGGAAATTC   1200

GGGAGAAAGC GGCGTCCTTG TCTTCATTGT TAGGTGTCGA TGCTGTCGAA AAGAATTGC    1260

GGCGTGTCGA ACCGGAACAT GAAGATAACA CCAGAGTTGA AGCCAGGGTA GAGGAATTGC   1320

AGAAGGCGCT GGAGAAGGCC GCGTCTGAGG CAAAGCAGCT CGTGGGGACC GCAGCAGGCG   1380

AAATAGAGGA AGGAGTAAAA GCGGATACTC AGGCTGTGCA AGATAGCTCG AAAGACGTGT   1440

TGACGAAGAG TCCAGTTGCG CTCGTGGAAG CCTTTAAAGC GATCCAGAGG GCTCTTCTTG   1500

AGGCGAAGAC AAAGGAACTA GTAGAGCCTA CGTCTAAAGA AGCGGAGGAA GCTCGTCAGA   1560

TCTTAGCGGA ACAGGCAGCT TGATTTCCCA AGGATGCAGT TAAAGATGGG GATGCATGAT   1620

AGGTAGCGCG CCCATTATCC CAATCCTTTA GCCGTCTACC GTGACGTGGA TCATTATAGG   1680

GGAAACAAGC ATTAGCAGAA TGATCGTGTA TCGCGGAACA CACGCATATC CGCACCAGTT   1740

TTTCTAACGT ATGGTGAATG GGTTCAAGTC TGGGTTCAAG GCGCAGTGTC TATGCAACAG   1800

CGCCGGTTTC TGCCCTTCGT TTTTGCACAT GTGCACAGGT ATGTACAGTG TTTATGTATA   1860

TGGGGCAGTG TGCGCTTCGT CAATGATGTA CAGAAAAAAA AAAAAAAA               1909
```

(2) INFORMATION FOR SEQ ID NO: 20:

(i) SEQUENCE CHARACTERISTICS:
        (A) LENGTH: 452 amino acids
        (B) TYPE: amino acid
        (D) TOPOLOGY: linear (ii) MOLECULE TYPE: peptide (xi) SEQUENCE DESCRIPTION: SEQ ID NO: 20:

```
Met Asp Cys Gly Gln Cys Arg Arg Gln Leu His Ala Ala Gly Val Leu
 1               5                  10                  15

Gly Leu Phe Val Thr Leu Ala Thr Ala Thr Val Gly Leu Ser Gln Arg
                20                  25                  30

Val Pro Glu Leu Pro Glu Val Glu Ser Phe Asp Glu Val Gly Thr Gly
            35                  40                  45

Ala Arg Arg Ser Gly Ser Ile Ala Thr Leu Leu Pro Gln Asp Ala Val
        50                  55                  60

Leu Tyr Glu Asn Ser Glu Asp Val Ala Val Pro Ser Asp Ser Ala Ser
 65                  70                  75                  80

Thr Pro Ser Tyr Phe His Val Glu Ser Pro Ala Ser Val Glu Ala
                85                  90                  95

Ala Thr Gly Ala Val Gly Glu Val Val Pro Asp Cys Glu Glu Arg Gln
            100                 105                 110

Glu Gln Gly Asp Thr Thr Leu Ser Asp His Asp Phe His Ser Gly Gly
        115                 120                 125
```

-continued

```
Thr Glu Gln Glu Gly Leu Pro Glu Thr Glu Val Ala His Gln His Glu
    130                 135                 140
Thr Glu Glu Gln Tyr Gly Thr Glu Gly Met Pro Pro Val Leu Pro
145                 150                 155                 160
Pro Ala Pro Val Val His Pro Arg Phe Ile Ala Val Pro Gly Pro Ser
                165                 170                 175
Val Pro Val Pro Phe Phe Ser Leu Pro Asp Ile His Pro Asp Gln Val
            180                 185                 190
Val Tyr Ile Leu Arg Val Gln Gly Ser Gly Asp Phe Asp Ile Ser Phe
        195                 200                 205
Glu Val Gly Arg Ala Val Lys Gln Leu Glu Ala Ile Lys Lys Ala Tyr
    210                 215                 220
Arg Glu Ala Thr Gly Lys Leu Glu Ala Asp Glu Leu Glu Ser Glu Arg
225                 230                 235                 240
Gly Pro Ala Val Ser Pro Arg Arg Leu Val Asp Leu Ile Lys Asp
                245                 250                 255
Asn Gln Arg Arg Leu Arg Ala Ala Leu Gln Lys Ile Lys Ile Gln Lys
            260                 265                 270
Lys Leu Glu Glu Ile Asp Asp Leu Leu Gln Leu Thr Arg Ala Leu Lys
    275                 280                 285
Ala Met Asp Ala Arg Leu Arg Ala Cys Gln Asp Met Ala Pro Ile Glu
    290                 295                 300
Glu Ala Leu Cys His Lys Thr Lys Ala Phe Gly Glu Met Val Ser Gln
305                 310                 315                 320
Lys Ala Lys Glu Ile Arg Glu Lys Ala Ala Ser Leu Ser Ser Leu Leu
                325                 330                 335
Gly Val Asp Ala Val Glu Lys Glu Leu Arg Arg Val Glu Pro Glu His
            340                 345                 350
Glu Asp Asn Thr Arg Val Glu Ala Arg Val Glu Glu Leu Gln Lys Ala
    355                 360                 365
Leu Glu Lys Ala Ala Ser Glu Ala Lys Gln Leu Val Gly Thr Ala Ala
    370                 375                 380
Gly Glu Ile Glu Glu Gly Val Lys Ala Asp Thr Gln Ala Val Gln Asp
385                 390                 395                 400
Ser Ser Lys Asp Val Leu Thr Lys Ser Pro Val Ala Leu Val Glu Ala
                405                 410                 415
Phe Lys Ala Ile Gln Arg Ala Leu Leu Glu Ala Lys Thr Lys Glu Leu
            420                 425                 430
Val Glu Pro Thr Ser Lys Glu Ala Glu Glu Ala Arg Gln Ile Leu Ala
        435                 440                 445
Glu Gln Ala Ala
450
```

TOXOPLASMA GONDII ANTIGENS, THE PREPARATION THEREOF AND THE USE THEREOF

This is a division of application Ser. No.09/461,240, filed Dec. 16, 1999, now U.S. Pat. No. 6,326,008 which is a division of application Ser. No. 08/301,162, filed Sep. 6, 1994, now U.S. Pat. No. 6,022,546 issued on Feb. 8, 2000, which is a continuation of application Ser. No. 08/167,128, filed Dec. 16, 1993, abandoned, which is a continuation of application Ser. No. 07/623,086, filed Dec. 6, 1980, abandoned, which claims priority under 35 U.S.C. §119 to application No. P3940598.2, filed Dec. 8, 1989, in the Federal Republic of GERMANY incorporated herein by reference.

The present invention relates to the identification of *Toxoplasma gondii* antigens and the preparation thereof by genetic engineering. A cDNA expression gene bank of this parasite was prepared. Recombinant clones which are of diagnostic interest were identified using a high-titer rabbit anti-*Toxoplasma gondii* serum, and isolated.

*Toxoplasma gondii* (*T.gondii*) is an obligatory intracellular single-cell parasite which is categorized as a coccidium. The parasite has a relatively wide range of hosts and can, in addition to very many mammals, also infect man. In the latter case there are two forms which differ from each other physiologically: "tachyzoites" reproduce asexually in a number of different cell types. This form is found exclusively in the acute stage of the infection. "Bradyzoites", in contrast, persist in cells of the cardiac and skeletal muscles and in cells of the central nervous system in encapsulated form and are responsible for a persistent immunity to reinfection. It is estimated that globally there are 500 million people who are chronically infected by *T.gondii*.

In healthy adults, a *T.gondii* infection normally has no symptoms with the exception of a slight swelling of the lymph nodes. During pregnancy and in immunosuppressed patients, however, an infection with this parasite may present particular problems. Thus there is the risk of an intra-uterine transfer of these parasites in pregnant women who have not acquired a protection from *T.gondii* by immunity. This leads to the infection of the fetus and may result in deformities of the child or the expulsion of the fetus.

Immunosuppressed patients frequently acquire an acute *T.gondii* infection as a result of the reactivation of enzysted "bradyzoites". In most cases this leads to cerebral toxoplasmosis (encephalitis), which may, under certain circumstances, be lethal. In addition to cerebral toxoplasmosis, *T.gondii* has also been mentioned as causative agent of eye diseases (chorioretinitis). These cases, too, are infections which can be blamed on a reactivation of "bradyzoites".

The clinical picture of toxoplasmosis often causes difficulties concerning differential diagnosis to the clinician so that the support by laboratory analyses in establishing the diagnosis is sought. The detection of antibodies and the determination of the titer or of the dynamics of the titer have therefore become essential tools for diagnosing toxoplasmosis. Methods for determining toxoplasma-specific immounoglobulins of the G and M class, such as indirect immunofluorescence (IF), complement fixation reaction (CF), indirect hemagglutination (IHA), latex agglutination (LA) and enzyme-linked immuno-assay (ELISA) are very common in the field of serodiagnosis but often have faults. For example these test methods vary very greatly as regards specificity and sensitivity. These differences are primarily caused by the preparation of the antigen which is used for the serological test. In most cases total cell antigen which contains a high proportion of unspecific cell components and is held responsible for the occurrence of false positive test results, is prepared. In addition, obtaining the antigens from infected mice holds the risk of infection for the person working in the laboratory.

In view of the specificity and sensitivity of a diagnostic of this type, it would thus be desirable to employ defined immunoreactive antigens which should additionally make it possible to distinguish between IgG- and IgM-specific anti-*T.gondii* antibodies.

A number of antigens of diagnostic interest have been described for *T.gondii* in the literature. For example Hughes describes in a review (Curr. Top. Microbiol. (1985), 120: 105–139) four major antigens which are potentially suitable for detecting anti-*T.gondii* antibodies of the IgG class, having molecular weights of 45, 32, 27 and 21 kilodalton (kD). Handman et al. (Immunol. (1980), 40: 579–588) and Potasman et al. (J. Infect. Diseases (1986), 154: 650–657) analyzed sera taken throughout the course of the disease of acutely infected *T.gondii* patients using Western blots and demonstrated that a 35 kD membrane antigen reacts with IgG antibody at a very early stage. Decoster et al. (Clinic. Exper. Immunol. (1988), 73: 376–382) describe four antigens of diagnostic interest, which, in contrast to the 35 kD antigen, can be isolated from the culture medium and have been termed "excreted-secreted antigens" (ES antigens) and which have molecular weights of 105, 97, 66 and 28.5 kD. IgG antibodies which react with antigens of 105, 97 and 28.5 kD seem to be good markers for a chronic toxoplasmosis. Similarly to the 35 kD antigen, the 97 kD antigen and the 66 kD antigen are recognized at a very early stage by IgM antibodies of acutely infected patients. It has to be pointed out that these antigens have not been sufficiently characterized by giving a molecular weight after electrophoretic fractionation because there usually are several proteins within one molecular weight range.

A 6 kD antigen is a further marker for acute toxoplasmosis (Ehrlich et al., (1983), Infect. Immun. 41: 683–690). In IgM Western blots, this antigen reacts relatively strongly. To date there are only very few data which might reveal the nature of this antigen.

Only very few *T.gondii* antigens have been biochemically characterized so far. The main surface protein P30 is an exception. This antigen is a glycoprotein which is anchored in the membrane via a glycolipid (Nagel et al., (1989), J. Biol. Chem. 264: 5569–5576). The diagnostic importance of this antigen is controversial since P30 also reacts with unspecific antibodies of the IgG class (Potasman et al., (1986), J. Clin. Microbiol. 24: 1050–1054).

The isolation and purification of individual antigens for the use in serodiagnosis often involves a considerable amount of work. Both the molecular weight data and the classification of the immunoreactivity of an antigen can substantially differ from case to case in conventionally purified antigen. Cloning and expressing such antigens and investigating the structure of the corresponding genes might not only improve the yield of purified antigen but should also contribute to the serological characterization and therefore to the investigation of the diagnostic relevance of the antigen. So far the structure of the genes of two immunologically interesting *T.gondii* antigens has been investigated. The complete nucleotide sequences of these antigens, which are P30 (Burg et al., (1988), J. Immunol. 141: 3584–3591) and a 28 kD antigen (Prince et al., (1989), Mol. Biochem. Parasitol. 34: 3–14), are known.

The object of the present invention is to prepare by genetic engineering defined antigens of *T.gondii*, which are suitable for diagnosis and prevention. It has been possible to successfully identify suitable T.gondii gene products from a lambda gt11 cDNA expression gene bank using a high-titer rabbit anti-T.gondii serum. Partial nucleic acid sequences, and aminoacid sequences derived therefrom, of 8 clones (F2, F28, F29, F34, F45, F61, F74 and F76) have been determined. All the abovementioned clones react in Western blots with human anti-T.gondii IgG sera. The clones F34, F61 and F76 additionally react with specific antibodies of the IgM class. The partial nucleotide sequences are listed in Tab. 1–8 (SEQ ID NOS:1–14) and, as far as they are apparent, also the translational reading frames (in Tab. 1–6 corresponding to SEQ ID NOS:1–12).

F61 (Tab. 1 SEQ ID NOS:1–2) is assigned to a protein having a molecular weight of 66 kD.

F34 (Tab. 2 SEQ ID NOS:3–4) belongs to a protein of about 68 kD.

F29 (Tab. 3 SEQ ID NOS:5–6) belongs to a protein of about 30 kD.

F28 (Tab. 4 SEQ ID NOS:7–8) belongs to a protein of about 28 kD.

F2 (Tab. 5 SEQ ID NOS:9–10) belongs to a protein of about 30 kD.

F76 (Tab. 6 SEQ ID NOS:11–12)belongs to a protein of about 35 kD.

F45 (Tab. 7 SEQ ID NOS:13) belongs to a protein of about 29 kD.

F74 (Tab. 8 SEQ ID NOS:14) belongs to a protein of about 64 kD.

With the aid of the partial sequences mentioned it is readily possible to clone the complete genes for the abovementioned partial sequences.

The partial sequences depicted in the Tables 1, 2 and 6 (SEQ ID NOS:1–12) were accordingly used to complete the coding cDNA regions of the genes belonging thereto. For this purpose, the cDNAs F61, F34 and F76 were radiolabeled and used as probes for screening the cDNA gene bank. The sequence from Table 1, F61, was used to isolate the cDNA of the P66 protein. The sequence from Tab. 2 (SEQ ID NOS:3–4), F34, was used for the isolation of the cDNA of the P68 protein. For the isolation of the cDNA of the P35 protein, the sequence from Tab. 6 (SEQ ID NOS:11–12), F76, was used. Recombinant clones having homologies to these sequences were isolated and characterized structurally by sequencing the inserted T.gondii-specific cDNA regions. The nucleotide sequences of the complete ranges of the structural genes of the P35, P66 and P68 proteins are depicted in the Tables 9–11 (SEQ ID NOS:15–20).

Immunologically reactive partial regions (immunogenic parts) are representatively described for P35, P66 and P68 in the Examples 6 and 7. Other immunogenic protein regions are tested or determined in an analogous way. The invention therefore relates to (a) the isolated inserted DNA sequences of the abovementioned clones, including the transcription products thereof and the remaining sequences to complete the particular structural genes, (b) DNA structures and vectors which contain, completely or in part, these sequences, (c) prokaryotic or eukaryotic cells which have been transformed with DNA of this type, (d) the polypeptides expressed by transformed cells of this type, or immunogenic parts thereof including the use thereof for diagnosis and therapy or prevention, (e) the amino-acid sequences (AS) belonging thereto, (f) antibodies against the polypeptides under (d), including the use thereof for the diagnosis and therapy or prevention of T.gondii infections, and (g) processes for the preparation by genetic engineering of the polypeptides mentioned under (d) or of immunogenic parts thereof.

The invention is furthermore described in the examples and the claims.

EXAMPLE 1

Construction of a lambda gt11-cDNA expression gene bank of T.gondii

1) Isolation of poly(A)$^+$ RNA

Confluent Hep-2 cell cultures were,infected with T.gondii parasites as described by Braveny et al. (Tropenmed. Parasitologie (1978), 29: 432–434). From day 4 after infection, the trophozoites were harvested by centrifugation of the culture supernatant. The total RNA from about 500 mg of pelleted T.gondii cells (wet weight) was isolated by a modified method of Chomczynski and Sacchi (1987), (Analytical Biochemistry, 162: 156–159) as follows: the cells were lysed in 20 ml of solution D (4M guanidinium isothiocyanate, 0.5% sarcosyl, 25 mM sodium citrate pH 7.0, 0.1 M mercaptoethanol) and, after addition of 2 ml of 2 M sodium acetate pH 4.0, 20 ml of phenol (saturated with water) and 4 ml of chloroform, the mixture was shaken vigorously and cooled on ice for 20 min. After a centrifugation step (30 min, 4° C., 15000 g), the RNA was precipitated from the aqueous phase with one volume of isopropanol for one hour at 4° C. and pelleted by subsequent centrifugation (20 min. 4° C., 15000 rpm). The pellet was resuspended in 600$\mu$l of solution D and the RNA was then centrifuged through a 5.7 M CsCl solution (3 ml) (12 h, 35000 rpm, 10° C.). The pellet was resuspended in 500 $\mu$l of double-distilled water (free of RNAse) and the RNA was precipitated again with 1/10 volume of sodium acetate and 2 volumes of ethanol for 2 h at −20° C. and pelleted by centrifugation (10 min, 14000 rpm, 4° C. in an Eppendorf centrifuge). Poly(A)$^+$ RNA was enriched via an oligo (dT)-cellulose (Pharmacia) column (0.5 g oligo dT-cellulose in 10 mM tris-HCl pH 7.5, 0.5 M KCl) as follows: LiCl (final concentration 0.5 M) was, after denaturing of the RNA solution (70° C., 10 min), added said and the mixture was run through oligo dT-cellulose column. After the column had been washed with 20 ml of binding buffer (10 mM tris-HCl pH 7.5, 0.5 M KCl), the poly(A)$^+$ RNA was eluted with 10 ml of double-distilled water and precipitated with 1/20 volume of 8 M LiCl and 2.5 volumes of ethanol at −20° C. for 4 h and then pelleted by centrifugation (6000 rpm, 4° C., 30 min), washed in 70% ethanol and dried.

2) cDNA synthesis

The synthesis of the cDNA was carried out by a modified method of Gubler (U. Gubler, (1988), Nucl. Acids. Res. 16: 2726): after denaturing 5 $\mu$l of T.gondii poly(A)$^+$ RNA (5 min, 70° C.), the synthesis of the first DNA strand is carried out in the presence of 50 mM tris-HCl pH 8.3, 75 mM KCl, 50 mM DTT, 15 mM MgCl$_2$, 0.5 [mM] dNTP, 5 $\mu$l of oligo dT primer (Boehringer, Mannheim) and 800 units of reverse transcriptase (BRL) in 50 $\mu$l of mixture at 37° C. for 1 h. The reaction is subsequently stopped at 70° C. for 10 min and, after additions of 8 $\mu$l of 1 M tris-HCl pH 7.5, 32 $\mu$l of 1 M KCl, 1.6 $\mu$l of 1 M MgCl$_2$, 1.6 $\mu$l of 1 M DTT, 50 units of E.coli DNA polymerase I (Boehringer, Mannheim), 3.5 units of RNAse H (Boehringer, Mannheim) in 320 $\mu$l final volume, the synthesis of the second DNA strand is started. The mixture is incubated at 16° C. for 1 hour and at 22° C. for 1 hour. The cDNA is then precipitated with two volumes of ethanol and 1/10 volume of sodium acetate at −70° C. for 10 min, pelleted by centrifugation and dried. The pellet is resuspended in 100 µl of T4 DNA polymerase buffer (20 mM (NH$_4$)$_2$SO$_4$, 50 mM tris-HCl pH 8.8, 10 MM MgCl$_2$, 50 µm dNTP) and the reaction filling the cDNA ends is started by addition of 10 units of T4 DNA polymerase (Boehringer, Mannheim). The mixture is incubated at 37° C. for 10 min and, after addition of 100 µl of phenol/chloroform (1:1), phenolized. The cDNA solution is then centrifuged through a Sephacryl S 200 column (Pharmacia). The cDNA is precipitated from the eluate with two volumes of ethanol and 1/10 volume of sodium acetate, centrifuged and dried.

3) Ligation of the cDNA with EcoRI adapter

The dried cDNA (1 µl) was resuspended in 30 µl of ligation buffer (30 mM tris-HCl pH 7.8, 10 mM MgCl$_2$, 0.5 mM ATP, 10 mM DTT), 40 pmol of EcoRI adapter (Promega) and 7.5 units of T4 DNA ligase were added and the mixture was incubated at 14° C. for 15 h. After inactivation of the ligase (10 min, 70° C.) and, after addition of 4 µl of kinase buffer (0.7 M tris-HCl pH 7.6, 0.1 M MgCl$_2$, 50 mM DTT), 2 µl of 0.1 mM ATP and 10 units of T4 polynucleotide kinase (Pharmacia), subsequent kinase treatment (30 min, 37° C.), the cDNA is again centrifuged through a Sephacryl S 200 column and then precipitated with ethanol and sodium acetate as described above.

4) Ligation of the cDNA with lambda gt11 EcoRI fragments, in vitro packaging and transfection of lambda gt11

For the ligation reaction, about 50 ng of kinase-treated cDNA were added to 1 µl of dephosphorylated lambda gt11 EcoRI fragments in 10 µl of mixture (66 mM tris-HCl pH 7.6, 6.6 mM MgCl$_2$, 1 mM ATP, 5 mM DTT) and, after addition of 3 Weiss units of T4 DNA ligase (Boehringer, Mannheim), the mixture was incubated at 14° C. for 15 h. 5 µl of this mixture are used in an in vitro packaging reaction which was carried out following the instructions of the packaging mix manufacturer (Giga Gold Mix, Stratagene).

After transfection of the *E.coli l strain* Y1090, the titer of recombinant phages was determined. A total of about $10^6$ recombinant phages was obtained.

EXAMPLE 2

Screening of the Lambda gt11 Expression Gene Bank Using a Hyperimmune Rabbit Anti-*T.gondii* Serum Anti-*E.coli* antibodies were initially adsorbed out of the rabbit anti-*T.gondii* serum by known methods (L. S. Osaki (1986), J. Immun. Method. 89: 213–219; Promega Biotec (1986), ProtoBlot Immunoscreening System, Technical Manual) in order to reduce nonspecific reactions in the immunoblot. For this purpose, lambda gt11 wild type phages were distributed on a total of 30 LB-agar plates at a density of $5 \times 10^4$ PFU in 9 ml of LB soft agar/0.4% maltose/10 mM MgSO$_4$ per 90 mm agar plate. After incubation at 37° C. for two hours, the plates were covered, in each case, with a dry round nitrocellulose filter equilibrated in 10 mM IPTG (isopropyl β-D-thiogalactopyranoside) and incubated for a further two hours. The filters were then turned over and again incubated on the agar for two hours. The filters were then incubated in 5% skimmed milk/powder/TBS buffer (TBS: 150 mM NaCl, 50 mM tris-HCl pH 8.0) at room temperature for 10 min and, after the transfer into 100 ml of rabbit serum diluted 1/100 in 5% skimmed powder milk/powder/TBS, incubated for four hours at room temperature. This pre-adsorbed, dilute serum was used both for the screening experiments and for Western blots. A total of $6 \times 10^5$ recombinant phages of the lambda gt11 cDNA bank was subjected to screening with this serum by the method of R. Y. Young and R. W. Davis (Proc. Natl. Acad. Sci. 80: 1194 (1983)). For this purpose, cells of a culture of the *E.coli* K12 strain Y1090 were, as described above, transfected with recombinant lambda gt11 phages ($3 \times 10^4$ phages/100 µl of Y1090 culture) and distributed on soft agar plates (20 plates total). After incubating for 2 h at 7° C., the plates were, in each case, covered with a dry nitrocellulose filter soaked in 10 mM IPTG and incubated for a further 2 h. After the position of the filters on the agar plates had been marked, the filters were carefully lifted off and shaken in 250 ml of 5% skimmed milk powder/TBS buffer for 10 min at room temperature. The filters were then transferred into fresh skimmed milk powder/TBS buffer and stored at 4° C. overnight.

After a further incubation of the filters in 250 ml of skimmed milk powder/TBS buffer, they were lightly shaken with 100 ml of the pre-adsorbed rabbit anti-*T.gondii* serum at room temperature for 1 h. Then the filters were washed three times with, in each case, 250 ml of TBS at room temperature for 10 min and shaken with 250 ml of anti-rabbit IgG/alkaline phosphatase IgG conjugate (Behringwerke, Marburg) diluted 1/300 in skimmed milk powder/TBS at room temperature for a further hour. After washing the filters (shaking three times with 250 ml of TBS at RT for 10 min each time), they were again incubated in 250 ml of a substrate solution for alkaline phosphatase (200 µg/ml p-toluidine salt of 5-bromo-4-chloro-indoxy phosphate (XP), (from Bachem, order no.: M1205), 500 µg/ml 4-nitrotetrazolium chloride blue (from Sigma, order no.: N6876)) for 15 min. Seropositive clones which can be recognized from the colored zone in the form of a ring around the phage plaque were matched up with the regions on the Petri dish, punched out using a Pasteur pipette and resuspended in 1 ml of SM buffer. Individual clones of the positive phage plaques were prepared in two further screening steps. A total of 83 seropositive clones was isolated. These clones were further characterized as follows.

1) Immunological characterization of the cDNA clones
2) Structural characterization of the cloned cDNA inserts
   a) DNA-DNA dot blot analyses
   b) Partial sequencing of the cDNA inserts in order to investigate the open reading frames
   c) Expression of the cloned cDNAs as a gene fusion with lacZ or lacZ' (partly deleted β-galactosidase derivative)
3) Immunological characterization of the seropositive cDNA clones The seropositive clones of the gene bank were characterized immunologically by means of "clone-specific" sera (this refers to sera which have been obtained from the polyclonal rabbit serum by adsorption on the recombinant fusion protein of a cDNA clone). These sera were prepared in accordance with Ozaki et al. (J. Immun. Method. 89: 213–219 (1986)) as follows: $5 \times 10^4$ PFU, in each case, of individual cDNA clones were, after adsorption to *E.coli* Y1090 cells, distributed on LB plates in soft agar and, after incubation for two hours, covered with, in each case, one nitrocellulose filter pretreated in 10 mM IPTG, and the treatment was continued as described in Example 2. Three filters, pretreated in this way, per clone were, in each case, incubated in the pre-adsorbed rabbit serum for four hours and then washed in 50 ml of TBS for 10 min (3 changes of buffer). The antibodies bound on the filters were washed off using a total of 15 ml of a 0.1 M glycine/HCl buffer (pH 2.5) at room temperature for 5 min and were neutralized with 3 ml of 1 M tris. skimmed milk powder was added to a final concentration of 5%. Monospecific sera were generated from 20 independent clones. The immuno-reactivity of these sera to recombinant protein of all seropositive clones was tested in dotblod experiments.

Clones whose recombinant proteins cross-reacted with a serum were grouped together in a clone group. In Southern dot blot analyses, $^{32}$P-labeled insert DNAs only showed a homology to the clone DNAs which were allocated to one group as a result of the above-described serological data. One clone ( was selected from each group and tested with human anti-*T.gondii* sera in a Western blot. For this purpose, the insert fragments of the clone DNAs were either subcloned into suitable expression vectors or the *E.coli* K12 strain Y1089 was lysogenized with the particular recombinant lambda gt11 derivatives.

EXAMPLE 4

Expression of the β-galactosidase Fusion Proteins

In order to investigate the immunoreactivity, the cDNA fragments of the lambda gt11 clones F2, F29, F28, F34, F61 and F76 were subcloned as gene fusions with a partly deleted lacZ derivative into vectors of the pSEM series (Knapp et al.,Biotechniques (1990), 8:280) and the expression of the fusion proteins was induced in *E.coli* W3110 lacI$^q$ L8 (Brent and Ptashne (1981) Proc. Natl. Acad. Sci., 78: 4204–4208) by addition of IPTG. For the expression of the fusion proteins of clones F45 and F74, the *E.coli* strain Y1089 was lysogenized with both lambda gt11 derivatives and then the fusion proteins were induced by known methods (Huynh et al. in: Glover, DNA Cloning Volume I, p. 49–78, IRL Press, Oxford (1985)). The proteins from total cell extracts were, after IPTG induction, fractionated electrophoretically in SDS PAGE (10%) and transferred onto nitrocellulose. The reactivity of the recombinant proteins was verified in a Western blot using human IgG and IgM sera. Finally, the clones characterized in this way were sequenced.

EXAMPLE 5

Sequencing of the cDNA Fragments

The sequencing of the cDNA fragments was carried out by the dideoxy method of Sanger (Proc. Natl. Acad. Sci. (1977), 74: 5463) using the "KS primer" (Promega). The insert fragments of the clones F2, F29, F34, F28, F45, F61, F74 and F76 were cleaved out of recombinant lambda gt11 DNA using EcoRI and, after insertion into the EcoRI cleavage site of the vector Bluescript KS, transformed into the *E.coli* strain XL1-Blue (Stratagene, San Diego). Single-stranded DNA of these recombinant plasmids was, after infection of the clones with the helper phage VCS, isolated by known methods (Stratagene, San Diego). Depending on the orientation of the cloned fragments, the sequence of the 5' or the 3' end of the cDNA is obtained. The Tables 1–8 (p. 5, corresponding to SEQ ID NOS:1–14), show the translational reading frames (Tab. 1–6, corresponding to SEQ ID NOS:1–12) and partial nucleotide sequences (Tab. 1–8, corresponding to SEQ ID NOS:1–14) of the abovementioned clones.

EXAMPLE 6

Diagnostic Suitability of the Recombinant *T.gondii* ntigens rP35, rP66 and rP68

Partial sequences from the region of the structural genes of the antigens P35, P66 and P68 were expressed in *E.coli* W3110 using pSEM expression vectors (Knapp et al., Biotechniques (1990), 8:280). The expression products are composed of an N-terminal β-galactosidase derivative of 375 aminoacids which contains an insert-specific fused portion at the C-terminus. The synthesis of the fusion proteins can be induced by IPTG as described in Knapp et al. (Biotechniques (1990), 8:280). For Westernblot experiments, total cell extracts of recombinant *E.coli* W3110 derivatives were, after IPTG induction, fractionated in SDS PAGE. The proteins were transferred to Nitrocellulose paper incubated with the specific serum sample and conjugate (antihuman IgG/alkaline phosphatase) and stained following a standard protocol (in: Sambrook et al.: Molecular Cloning, Cold Spring Harbor Laboratory Press (1989)). The following sections of the abovementioned *T.gondii* proteins were expressed:

rP35: base pairs 363–527*; contained in the hybrid plasmid pPS76 rP66: base pairs 176–1927*; contained in the hybrid plasmid pPS34 rP66: base pairs 1–2074*; contained in the hybrid plasmid pPS61

(* the coordinates of the nucleotide sequences refer to the data in the Tables 9–11, corresponding to SEQ ID NOS:15–20).

The reactivity of specific IgG and IgM antibodies from human sera of patients having acute or chronic *T.gondii* infections was investigated in Western blot experiments. A summary of the results of these investigations is shown in Table 12. Thus all three hybrid proteins, rP35, rP66 and rP68, are suitable for the detection of specific IgG antibodies. Particular emphasis has to be laid on rP35:25/26 sera reacted with the hybrid protein in IgG Western blots; using rP68, specific IgG antibodies were recognized in 27/31 sera. Both fusion proteins, rP35 and rP68, without exception reacted with IgG anti-*T.gondii* antibodies from acute sera (n=21) which had a detectable specific IgM antibody titer. For this reason both rP35 and rP68 are particularly suitable as markers for the detection of IgG anti-*T.gondii* antibodies in the acute phase of toxoplasmosis.

rP66 reacted with most of the 21 sera tested in the IgM blot and is thus suitable as a marker for the detection of specific antibodies of this immunoglobulin class.

EXAMPLE 7

Suitability of the Recombinant *T.gondii* Proteins rP35 and rP68 in ELISAs

The reactivity of the recombinant *T.gondii* proteins rP35 and rP68 with specific IgG antibodies was investigated in ELISAs. The two proteins were used as solid phase antigens either together or each by itself for coating ELISA plates. The two hybrid proteins were isolated from *E.coli*; as follows:

An overnight culture of the recombinant *E.coli* strain W3110 containing the plasmids pPS76 or pPS34 was diluted 1/50 in 2 1 of L-broth/100 mg/ml ampicillin and, with vigorous shaking, grown to a 0D600=0.7 at 37° C. After the addition of IPTG (final concentration 1 mM), the cultures were shaken vigorously at 37° C. for a further 3 h, spun down and the cell pellet was taken up in 150 mM NaCl/50 mM tris-HCl pH 8.0/1 mg/ml lysozyme and incubated at 37° C. for 10 min. For cell breakage, the cell suspension was treated 2× in a French press. The ruptured cells were centrifuged (10000 rpm, 10 min, 4° C.) and the pellet containing the fusion protein present as sparingly soluble inclusion bodies was washed with a succession of urea solutions of varying concentrations (1 M–6 M urea). In this procedure, first the pellet was stirred in 30 ml of 1 M urea/10 mM tris/1 mM EDTA pH 8.0 (TE) at RT for 1 h. After centrifuging (10000 rpm, 10 min, 4° C.), the pellet was taken up as described above in 2 M urea and incubated. These incubations were then continued with 3 M, 4 M, 5 M and 6 M urea. The supernatants after the centrifugation steps were stored and the proteins soluble therein analyzed in SDS PAGE. Those supernatants which, in addition to the fusion protein, only contained slight contaminations of E.coli protein (about 75% fusion protein) were used further for coating the ELISA plates. These supernatants were dialyzed against 1 M urea/0.1% SDS at 4° C. for 72 h. For coating the ELISA plates, the protein concentration of the dialyzed samples was adjusted to 2 µg/ml with PBS pH 7.0. The coating was carried out at 4° C. overnight using 100 µl/well. The plates were then washed 3× with AP washing buffer (Behring, order no.: 1353115) before the serum samples were applied to the plates.

Adsorption of anti-E.coli antibodies in serum samples: First, anti-E.coli antibodies were removed from the serum samples. For this purpose, the cells of an E.coli W3110 overnight culture were spun down and the pellet was resuspended in 5 ml of PBS pH 7.0. The cells were lyzed by ultrasound (sonication 3×, Branson sonifier set to 7) and, after addition of DNAse I (final concentration 1 µl/ml), incubated at 37° C. for 10 min. Human serum and lysate antigen were mixed in a ratio of 1:1, diluted 1/50 in PBS pH 7,0 and shaken at RT for 30 min. After the centrifugation, 5% skimmed milk/PBS pH 7,0 were added to the supernatant (final concentration 1%), 100 µl/well thereof were incubated on ELISA plates at 37° C. for 1 h and these were washed 3× with AP washing buffer.

Then 100 µl/well of the anti-human IgG/AP conjugate (Behring order no.: OSDH 04/05) prediluted 1/70 in AP conjugate dilution buffer (Behring order no.: 1332115) were incubated at 37° C. for 1 h. The plates were washed 3× with AP washing buffer and incubated with 100 µl/well of AP substrate solution (Behring AP substrate tablets, order no.: OSCX 96; Behring 10% diethanolamine, order no.: 0243115; substrate solution: 2 tablets in 10 ml of 10% diethanolamine) at 37° C. for 30 min and the optical density of the substrate solution was determined at 405 nm.

9 sera of a seroconverted patient (patient A1) were included in the investigations. The serum samples were taken from the donor on the following days: A, 9.8.1988; B, 18.8.1988; C, 29.8.1988; D, 12.10.1988; E, 2.12.1988; F, 13.1.1989; G, 28.2.1989; H, 12.5.1989; I, 17.7.1989. The infection took place on 31.7.1988, as can be proved. As can be seen from Tab. 13, human serum B, which was taken after day 17, shows specific IgG antibodies to rP35 and rP68 already. In contrast, this serum sample was negative in a classical, nonrecombinant ELISA system (IgG detection).

Moreover 30 human sera of donors with acute toxoplasmosis, which sera contained specific IgM antibodies, were analyzed for IgG antibodies to rP35 and rP68 in an ELISA. These human sera reacted without exception in the ELISA which contained both recombinant antigens rP35 and rP68 on the solid phase. Additionally 150 sera from blood donors were analyzed for specific IgG anti-rP35 and anti-rP68 antibodies. The same antisera were analyzed in the Enzygnost® toxoplasmosis (IgG; manufacturer: Behringwerke AG) for specific IgG antibodies and the results of the two tests were compared with each other. This showed that the sera which were positive in the Enzygnost® were also positive in the rP35/rP68 ELISA. For the anti-T.gondii-negative sera also, the data from the rP35/rP68 ELISA were consistent with those from the Enzygnost® ELISA.

TABLE 1a (SEQ ID NOS:1-2)

```
CATATACTGCACTGACTTCGACACCATGGAGCAAAGGCTGCCAATTATTCTACTTGTTCT
---------+---------+---------+---------+---------+---------   50
GTATATGACGTGACTGAAGCTGTGGTACCTCGTTTCCGACGGTTAATAAGATGAACAAGA

I   Y   C   T   D   F   D   T   M   E   Q   R   L   P   I   I   L   L   V   L -

CTCTGTGTTCTTCAGTTCAACCCCAAGCGCCGCCCTTTCGAGTTACAATGGAGTCCCCGC
---------+---------+---------+---------+---------+---------+  120
GAGACACAAGAAGTCAGTTGGGGGTTCGCGGCGGGAAAGCTCGGTGTTACCTCAGGGGCG

S   V   F   F   S   S   T   P   S   A   A   L   S   S   H   N   G   V   P   A -

TTATCCATCGTATGCACAGGTATCGCTCTCTTCCAACGGCGAGCCACGGCACAGGGGCAT
---------+---------+---------+---------+---------+---------+  180
AATAGGTAGCATACGTGTCCATAGCGAGAGAAGGTTGCCGCTCGGTGCCGTGTCCCCGTA

Y   P   S   Y   A   Q   V   S   L   S   S   N   G   E   P   R   H   R   G   I -

ACGCGGCAGCTTCCTCATGTCCGTAAAGCCACACGCAAACGCTGATGACTTCGCCTCCGA
---------+---------+---------+---------+---------+---------+  240
TGCGCCGTCGAAGGAGTACAGGCATTTCGGTGTGCGTTTGCGACTGCTGAAGCGGAGGCT

R   G   S   F   L   M   S   V   K   P   H   A   N   A   D   D   F   A   S   D -

CGACAACTACGAACCGCTGCCGAGTTTCGTGGAAGCTCCTGTCAGAGGCCCGGACCAAGT
---------+---------+---------+---------+---------+---------+  300
GCTGTTGATGCTTGGCGACGGCTCAAAGCACCTTCGAGGACAGTCTCCGGGCCTGGTTCA

D   N   Y   E   P   L   P   S   F   V   E   A   P   V   R   G   P   D   Q   V -

CCCTGCCAGAGGAGAAGCTGCTCTTGTCACAGAGGAGACTCCAGCGCAACAGCCGGCGGT
---------+---------+---------+---------+---------+---------+  360
GGGACGGTCTCCTCTTCGACGAGAACAGTGTCTCCTCTGAGGTCGCGTTGTCGGCCGCCA
```

TABLE 1a-continued (SEQ ID NOS:1-2)

```
  P   A   R   G   E   A   A   L   V   T   E   E   T   P   A   Q   Q   P   A   V  -
GGCTCTAGGCAGTGCAGAAGGGGAGGGGACTCCACCTACTGAATCCGCCTCCGAAAATTC
---------+---------+---------+---------+---------+---------+ 420
CCGAGATCCGTCACGTCTTCCCCTCCCCTGAGGTGGATGACTTAGGCGGAGGCTTTTAAG

A   L   G   S   A   E   G   E   G   T   P   P   T   E   S   A   S   E   N   S  -
TGAAGATGATGACACGTTTCACGATGCCCTCCAAGAGCTTCCAGAGGATGGCCTCGAAGT
---------+---------+---------+---------+---------+---------+ 480
ACTTCTACTACTGTGCAAAGTGCTACGGGAGGTTCTCGAAGGTCTCCTACCGGAGCTTCA

E   D   D   D   T   F   H   D   A   L   Q   E   L   P   E   D   G   L   E   V  -
GCGCCCACCAAATGCACAGGAGCTGCCCCCACCAAATGTACAGGAGCTGCCCCCACCAAA
---------+---------+---------+---------+---------+---------+ 540
CGCGGGTGGTTTACGTGTCCTCGACGGGGGTGGTTTACATGTCCTCGACGGGGGTGGTTT

R   P   P   N   A   Q   E   L   P   P   P   N   V   Q   E   L   P   P   P   N  -
TGTACAGGAGCTGCCCCCACCAACTGAACAGGAGCTGCCCCCACCAACTGAACAGGAGCT
---------+---------+---------+---------+---------+---------+ 600
ACATGTCCTCGACGGGGGTGGTTGACTTGTCCTCGACGGGGGTGGTTGACTTGTCCTCGA

V   Q   E   L   P   P   P   T   E   Q   E   L   P   P   P   T   E   Q   E   L  -
```

TABLE 1b (SEQ ID NOS:1-2)

```
GCCCCCACCAACTGAACAGGAGCTGCCCCCACCAACTGAACAGGAGCTAGCCCCATCAAC
---------+---------+---------+---------+---------+---------+ 660
CGGGGGTGGTTGACTTGTCCTCGACGGGGGTGGTTGACTTGTCCTCGATCGGGGTAGTTG

P   P   P   T   E   Q   E   L   P   P   P   T   E   Q   E   L   A   P   S   T  -
TGAACAGGAGCTGCCCCCACCAGTGGGCGAAGGTCAAGTCTGCAAAGTCCCTGGGGAACA
---------+---------+---------+---------+---------+---------+ 720
ACTTGTCCTCGACGGGGGTGGTCACCCGCTTCCAGTTCAGACGTTTCAGGGACCCCTTGT

E   Q   E   L   P   P   P   V   G   E   G   Q   R   L   Q   V   P   G   E   H  -
TGGGCCACAGGGGCCCCCATACGATGATCAGCAGCTGCTTTTAGAGCCTACGGAAGAGCA
---------+---------+---------+---------+---------+---------+ 780
ACCCGGTGTCCCCGGGGGTATGCTACTAGTCGTCGACGAAAATCTCGGATGCCTTCTCGT

G   P   Q   G   P   P   Y   D   D   Q   Q   L   L   L   E   P   T   E   E   Q  -
ACAGGAGGGCCCTCAGGAGCCGCTGCCACCGCCGCCGCCCCCGACTCGGGGCGAACAACC
---------+---------+---------+---------+---------+---------+ 840
TGTCCTCCCGGGAGTCCTCGGCGACGGTGGCGGCGGCGGGGGCTGAGCCCCGCTTGTTGG

Q   E   G   P   Q   E   P   L   P   P   P   P   P   P   T   R   G   E   Q   P  -
CGAAGGACAGCAGCCGCAGGGACCAGTTCGTCAAAATTTTTTTCGTCGGGCGTTGGGGGC
---------+---------+---------+---------+---------+---------+ 900
GCTTCCTGTCGTCGGCGTCCCTGGTCAAGCAGTTTTAAAAAAAGCAGCCCGCAACCCCCG

E   G   Q   Q   P   Q   G   P   V   R   Q   N   F   F   R   R   A   L   G   A  -
CGCAAGAAGCCGATTAGGAGGTGCACGACGAAATGTCAGTGGGGTGTTCCGAAGAGTCAG
---------+---------+---------+---------+---------+---------+ 960
GCGTTCTTCGGCTAATCCTCCACGTGCTGCGGTACAGTCACCCCACAAGGCTTCTCAGTC

A   R   S   R   F   G   G   A   R   R   H   V   S   G   V   F   R   R   V   R  -
AGGTGGTTTGAACCGTATAGTAGGTGGAGTGAGGAGTGGTTTCAGGCGTGCAAGAGAAGG
---------+---------+---------+---------+---------+---------+ 1020
TCCACCAAACTTGGCATATCATCCACCTCACTCCTCACCAAAGTCCGCACGTTCTCTTCC

G   G   L   N   R   I   V   G   G   V   R   S   G   F   R   R   A   R   E   G  -
AGAAGGTTTAGGTAGGAGTTTCTATCGTGTAAGAGGAGCTGTCAGTAGCGGTCGTAGGCG
```

TABLE 1b-continued

(SEQ ID NOS:1–2)

```
---------+---------+---------+---------+---------+---------+ 1080
ACAGCAACCCCCTCAGGCAGCAAATTGTTCACCACGGTGAGACCCAGAGCCAGCACATCC

V   V   G   G   V   R   R   L   T   S   G   A   S   L   G   L   G   R   V   G -

AGAAGGTTTAGGTAGGAGTTTCTATCGTGTAAGAGGAGVTGTCAGTAGCGGTCGTAGGCG
---------+---------+---------+---------+---------+---------+ 1140
TCTTCCAAATCCATCCTCAAAGATAGCACATTCTCCTCGACAGTCATCGCCAGCATCCGC

E   G   L   G   R   S   F   Y   R   V   R   G   A   V   S   S   G   R   R   R -

TGCAGCAGATGGTGCCAGCAATGTAAGAGAAAGATTCGT
---------+---------+---------+--------- 1179
ACGTCGTCTACCACGGTCGTTACATTCTCTTTCTAAGCA
  A   A   D   G   A   S   N   V   R   E   R   F
```

TABLE 2a

(SEQ ID NOS:3–4)

```
CTGAACAGGAGGGTTTGCCGGAAACAGAGGTGGCGCATCAGCATGAGACAGAAGAACAGT
---------+---------+---------+---------+---------+---------+  60
GACTTGTCCTCCCAAACGGCCTTTGTCTCCACCGCGTAGTCGTACTCTGTCTTCTTGTCA

E   Q   E   G   L   P   E   T   E   V   A   H   Q   H   E   T   E   E   Q   Y -

ACGGGACTGAAGGGATGCCCCCCCCTGTTCTGTTCTGCCACCTGCACCGGTAGTCCATCC
---------+---------+---------+---------+---------+---------+ 120
TGCCCTGACTTCCCTACGGGGGGGGACAAGACGGTGGACGTGGCCATCAGGTAGGCGCAA

G   T   E   G   M   P   P   P   V   L   P   P   A   P   V   V   H   P   R   F -

TTATTGCAGTACCAGGGCCGTCGGTGCCTGTTCCATTTTTCAGTTTGCCAGACATCCACC
---------+---------+---------+---------+---------+---------+ 160
AATAACGTCATGGTCCCGGCAGCCACGGACAAGGTAAAAAGTCAAACGGTCTGTAGGTGG

I   A   V   P   G   P   S   V   P   V   P   F   F   S   L   P   D   I   H   P -

CGGATCAGGTTGTGTATATTCTAAGGGTTCAGGGATCTGGGGACTTCGACATCAGTTTCG
---------+---------+---------+---------+---------+---------+ 240
GCCTAGTCCAACACATATAAGATTCCCAAGTCCCTAGACCCCTGAAGCTGTAGTCAAAGC

D   Q   V   V   Y   I   L   R   V   Q   G   S   G   D   F   D   I   S   F   E -

AAGTTGGCCGAGCTGTGAAGCAGTTGGAAGCCATCAAGAAAGCATACAGAGAAGCCACCG
---------+---------+---------+---------+---------+---------+ 300
TTCAACCGGCTCGACACTTCGTCAACCTTCGGTAGTTCTTTCGTATGTCGCTTCGGTGGC

V   G   R   A   V   K   Q   L   E   A   I   K   K   A   Y   R   E   A   T   G -

GGAAGCTAGAAGCAGACGAGCTTGAGTCAGAAAGGGGACCTGCTGTTTCACCTCGACGAA
---------+---------+---------+---------+---------+---------+ 360
CCTTCGATCTTCGTCTGCTCGAACTCAGTCTTTCCCCTGGACGACAAAGTGGAGCTGCTT

K   L   E   A   D   E   L   E   S   E   R   G   P   A   V   S   P   R   R   R -

GGCTGGTTGACCTGATCAAAGATAACCAGCGACGACTCAGGGCGGCGCTTCAGAAGATAA
---------+---------+---------+---------+---------+---------+ 420
CCGACCAACTGGACTACTTTCTATTGGTCGCTGCTGAGTCCCGCCGCGAAGTCTTCTATT

L   V   D   L   I   K   D   N   Q   R   R   L   R   A   A   L   Q   K   I   K -

AGATACAGAAAAAGTTGGAGGAGATTGATGACTTACTTCAGCTGACACGCGCACTGAAGG
---------+---------+---------+---------+---------+---------+ 480
TCTATGTCTTTTTCAACCTCCTCTAACTACTGAATGAAGTCGACTGTGCGCGTGACTTCC

I   Q   K   K   L   E   E   I   D   D   L   L   Q   L   T   R   A   L   K   A -

CCATGGATGCCCGTCTGAGAGCCTGCCAGGATATGGCACCGATTGAGGAGGCGCTGTGTC
---------+---------+---------+---------+---------+---------+ 540
GGTACCTACGGGCAGACTCTCGGACGGTCCTATACCGTGGCTAACTCCTCCGCGACACAG

M   D   A   R   L   R   A   C   Q   D   M   A   P   I   E   E   A   L   C   H -
```

TABLE 2a-continued
(SEQ ID NOS:3–4)

```
ACAAGACGAAGGCGTTTGGAGAAATGGTGTCCCAGAAAGCCAAGGAAATTCGGGAGAAAG
---------+---------+---------+---------+---------+---------+ 600
TGTTCTGCTTCCGCAAACCTCTTTACCACAGGGTCTTTCGGTTCCTTTAAGCCCTCTTTC

K  T  K  A  F  G  E  M  V  S  Q  K  A  K  E  I  R  E  K  A -
```

TABLE 2b
(SEQ ID NOS:3–4)

```
CGGCGTCCTTGTCTTCATTGTTAGGTGTCGATGCTGTCGAAAAAGAATTGCGGCGTGTCG
---------+---------+---------+---------+---------+---------+ 660
GCCGCAGGAACAGAAGTAACAATCCACAGCTACGACAGCTTTTTCTTAACGCCGCACAGC

A  S  L  S  S  L  L  G  V  D  A  V  E  K  E  L  R  R  V  E -

AACCGGAACATGAAGATAACACCAGAGTTGAAGCCAGGGTAGAGGAATTGCAGAAGGCGC
---------+---------+---------+---------+---------+---------+ 720
TTGGCCTTGTACTTCTATTGTGGTCTCAACTTCGGTCCCATCTCCTTAACGTCTTCCGCG

P  E  H  E  D  N  T  R  V  E  A  R  V  E  E  L  Q  K  A  L -

TGGAGAAGGCCGCGTCTGAGGCAAAGCAGCTCGTGGGGACCGCAGCAGGCGAAATAGCGG
---------+---------+---------+---------+---------+---------+ 780
ACCTCTTCCGGCGCAGACTCCGTTTCGTCGAGCACCCCTGGCGTCGTCCGCTTTATCGCC

E  K  A  A  S  E  A  K  Q  L  V  G  T  A  A  G  E  I  E  E -

AAGGAGTAAAAGCGGATACTCAGGCTGTGCAAGATAGCTCGAAAGACGTGTTGACGAAGA
---------+---------+---------+---------+---------+---------+ 840
TTCCTCATTTTCGCCTATGAGTCCGACACGTTCTATCGAGCTTTCTGCACAACTGCTTCT

G  V  K  A  D  T  Q  A  V  Q  D  S  S  K  D  V  L  T  K  S -

GTCCAGTTGCGCTCGTGGAAGCCTTTAAAGCGATCCAGCGGGCTCTTCTTGAGGCGAAGA
---------+---------+---------+---------+---------+---------+ 900
CAGGTCAACGCGAGCACCTTCGGAAATTTCGCTAGGTCGCCCGAGAAGAACTCCGCTTCT

P  V  A  L  V  E  A  F  K  A  I  Q  R  A  L  L  E  A  K  T -

CAAAGGAACTAGTAGAGCCTA
---------+---------+- 921
GTTTCCTTGATCATCTCGGAT

K  E  L  V  E  P
```

TABLE 3
(SEQ ID NOS:5–6)

```
GCCGGAACTAACAGAGGAGCAACAGAGAGGCGACGAACCCCTAACCACCGGCCAGAATGT
---------+---------+---------+---------+---------+---------+ 60
CGGCCTTGATTGTCTCCTCGTTGTCTCTCCGCTGCTTGGGGATTGGTGGCCGGTCTTACA

P  E  L  T  E  E  Q  Q  R  G  D  E  P  L  T  T  G  Q  N  V -

GGGCACTGTGTTAGGCTTCGCAGCGCTTGCTGCTGCCGCAGCGTTCCTTGGCSTGGGTCT
---------+---------+---------+---------+---------+---------+ 120
CCCGTGACACAATCCGAAGCGTCGCGAACGACGACGGCGTCGCAAGGAACCGTACCCAGA

G  T  V  L  G  F  A  A  L  A  A  A  A  F  L  G  M  G  L -

CACGAGGACGTACCGACATTTTTCCCCACGCAAAAACAGATCACGGCAGCCTGCACTCGA
---------+---------+---------+---------+---------+---------+ 180
GTGCTCCTGCATGGCTGTAAAAAGGGGTGCGTTTTTGTCTAGTGCCGTCGGACGTGAGCT
```

TABLE 3-continued

(SEQ ID NOS:5-6)

```
 T  R  T  Y  R  H  F  S  P  R  K  N  R  S  R  Q  P  A  L  E -

GCAAGAGGTGCCTGAATCAGGCGAAGATGGGGAGGATGCCCGCCAG
---------+---------+---------+---------+---------+------  226
CGTTCTCCACGGACTTAGTCCGCTTCTACCCCTCCTACGGGCGGTC
 Q  E  V  P  E  S  G  E  D  G  E  D  A  R  Q
```

TABLE 4

(SEQ ID NOS:7-8)

```
CCGTTGCTGTCGGGGTGCTATCTTCTCCCACCTTTTATCAGTTAAGTTGTACAGTGAGTG
---------+---------+---------+---------+---------+---------+  60
GGCAACGACAGCCCCACGATAGAAGAGGGTGCAAAATAGTCAATTCAACATGTCACTCAC

R  C  C  R  G  A  I  F  S  H  L  L  S  V  K  L  Y  S  E  C -

TCAGCTTGTTCGACACGTCTGTATAGACGCAACTCGGTTTGCTTGTGTTGTTTGGTGGGC
---------+---------+---------+---------+---------+---------+ 120
AGTCGAACAAGCTGTGCAGACATATCTGCGTTGAGCCAAACGAACACAACAAACCACCG

Q  L  V  S  T  R  L  Y  R  R  N  S  V  C  L  C  C  L  V  A -

TGGCCAAATCAAAGGCTATTCATTTTTCACTTGCTGTTGTTCTTTGAAGAAATCAAGCAA
---------+---------+---------+---------+---------+---------+ 180
ACCGGTTTAGTTTCCGATAAGTAAAAAGTGAACGACAACAAGAAACTTCTTTAGTTCGTT

G  Q  I  K  G  Y  S  F  F  T  C  C  C  S  L  K  K  S  S  K -

GATGGTGCGTGTGAGCGCTATTGTCGGAGCTGCTGCATCGGTGTTCGTGTGCCTGTCTGC
---------+---------+---------+---------+---------+---------+ 240
CTACCACGCACACTCGCGATAACAGCCTCGACGACGTAGCCACAAGCACACGGACAGACG

M  V  R  V  S  A  I  V  G  A  A  A  S  V  F  V  C  L  S  A -

CGGCGCTTACGCTGCCGAAGGCGGCGACAACCAGTCGAGCGCCGTCTCAGATCGGGCGTC
---------+---------+---------+---------+---------+---------+ 300
GCCGCGAATGCGACGGCTTCCGCCGCTGTTGGTCAGCTCGCGGCAGAGTCTAGCCCGCAG

G  A  Y  A  A  E  G  G  D  N  Q  S  S  A  V  S  D  R  A  S -

TCTCTTTGGTTTGCTGAGTGGAGGGACAGGGCA
---------+---------+---------+---  333
AGAGAAACCAAACGACTCACCTCCCTGTCCCGT

L  F  G  L  L  S  G  G  T  G
```

TABLE 5

(SEQ ID NOS:9-10)

```
CAGTTTCGCGCGTCCCGTTTCCACGGACAAAATGGCAATGAAATACGTCGCTGCTTACCT
---------+---------+---------+---------+---------+---------+  60
GTCAAAGCGCGCAGGGCAAAGGTGCCTGTTTTACCGTTACTTTATGCAGCGACGAATGGA

S  F  A  R  P  V  S  T  D  K  M  A  M  K  Y  V  A  A  Y  L -

GATGGTGGTGCTGTCGGGAACCGACACTCCGACCAAGAAGCAGGTTGAGAAAACCCTCTC
---------+---------+---------+---------+---------+---------+ 120
CTACCACCACGACAGCCCTTGGCTGTGAGGCTGGTTCTTCGTCCAACTCTTTTGGGAGAG

M  V  V  L  S  G  T  D  T  P  T  K  K  Q  V  E  K  T  L  S -

CTCTGTGGGTATTGATGTTGAAGACGACATCATGGACACCTTCTTCAAAGCTGTCGAAGG
---------+---------+---------+---------+---------+---------+ 180
GAGACACCCATAACTACAACTTCTGCTGTAGTACCTGTGGAAGAAGTTTCGACAGCTTCC
```

TABLE 5-continued (SEQ ID NOS:9-10)

```
  S   V   G   I   D   V   E   D   D   I   M   D   T   F   F   K   A   V   E   G -
AAAGACCCCCCACGAGCTGATTGCCGCGGGTATGGAGAAGCTCCAGAAGGTACCTTCTGG
---------+---------+---------+---------+---------+---------+ 240
TTTCTGGGGGTGCTCGACTAACGGCGCCCATACCTCTTCGAGGTCTTCCATGGAAGACC

K   T   P   H   E   L   I   A   A   G   M   E   K   L   Q   K   V   P   S   G -
TGGTGTCGCTGCTGCTGCTGCTCCTGCTGCTGGCGCTGCCGATGCTGGTGCGGGTGCTGC
---------+---------+---------+---------+---------+---------+ 300
ACCACAGCGACGACGACGACGAGGACGACGACCGCGACGGCTACGACCACGCCCACGACG

G   V   A   A   A   A   A   P   A   A   G   A   A   D   A   G   A   G   A   A -
TGGTGCGAAGAAGGAGGAGGAAAAGAAGGAGGAAGAGGAGGAGGAAGACGACATG
---------+---------+---------+---------+---------+----- 355
ACGACGATTCTTCCTCCTCCTTTTCTTCCTCCTTCTCCTCCTCCTTCTGCTGTAC

A   A   K   K   E   E   E   K   K   E   E   E   E   E   D   D   M
```

TABLE 6

(SEQ ID NOS:11-12)

```
GCCACAGCCAGAGATACCGCCTGTTCATCGGCCGCCGCCTCCGGGTTTCCGTCCCGAAGT
---------+---------+---------+---------+---------+---------+ 60
CGGTGTCGGTCTCTATGGCGGACAAGTAGCCGGCGGCGGAGGCCCAAAGGCAGGGCTTCA

P   Q   P   E   I   P   P   V   H   R   P   P   P   P   G   F   R   P   E   V -
GGCTCCCGTGCCCCCGTATCCAGTGGGCACTCCAACGGGCATGCCCCAGCCGGAGATACC
---------+---------+---------+---------+---------+---------+ 120
CCGAGGGCACGGGGGCATAGGTCACCCGTGAGGTTGCCCGTACGGGGTCGGCCTCTATGG

A   P   V   P   P   Y   P   V   G   T   P   T   G   M   P   Q   P   E   I   P -
GGCAGTTCACCATCCGTTCCCCTACGTTACGACAACCACGACAG
---------+---------+---------+---------+---- 164
CCGTCAAGTGGTAGGCAAGGGGATGCAATGCTGTTGGTGCTGTC

A   V   H   H   P   F   P   Y   V   T   T   T   T   T
```

TABLE 7

```
(SEQ ID NO:13)
ATATATGTGTCTCGTGCTTGAGTGTGTTCTTTGTATGATCAAAACTCGTTAAAATGCGCA
---------+---------+---------+---------+---------+---------+ 60
TATATACACAGAGCACGAACTCACACAAGAAACATACTAGTTTTGAGCAATTTTACGCGT

CGTTACCGCATGGGTAGTAGTTCGAGACAGCTTGTGTGTACCTGAGGGGCCGCGTGTTGC
---------+---------+---------+---------+---------+---------+ 120
GCAATGGCGTACCCATCATCAAGCTCTGTCGAACACACATGGACTCCCCGGCGCACAACG

CAAAAGTGCCTAGTCTTACACGGCCGACAAGAGGGTTCCTCGGTTCTTCTCTGCGTTCTT
---------+---------+---------+---------+---------+---------+ 180
GTTTTCACGGATCAGAATGTGCCGGCTGTTCTCCCAAGGAGCCAAGAAGAGACGCAAGAA

CCTTCTCCCATCCGATTCTTCAAGTTCTGAACAAATCTGTCGTGTCTCGACTGATGTGCG
---------+---------+---------+---------+---------+---------+ 240
GGAAGAGGGTAGGCTAAGAAGTTCAAGACTTGTTTAGACAGCACAGAGCTGACTACACGC

TGCGTTTTGA
---------+ 250
ACGCAAAACT
```

TABLE 8

(SEQ ID NO:14)
```
GGAATTCTTGTTACGCGGTCAGATGTTTCTTGAGTAGTGAATCAAAATGTATTATGGTGT
---------+---------+---------+---------+---------+---------+  60
CCTTAAGAACAATGCGCCAGTCTACAAAGAACTCATCACTTAGTTTTACATAATACCACA

AATCCTGTCAGTTTTATACGTATTGTCATACGTCCACGCATCTCACGTACGGGCGCGAAC
---------+---------+---------+---------+---------+---------+ 120
TTAGGACAGTCAAAATATGCATAACAGTATGCAGGTGCGTAGAGTGCATGCCCGCGCTTG

GCAGCAAGTGACGAGAGATCATCCCACTCGTTTGGTGACGCTGCAAAATACAAGTGTATT
---------+---------+---------+---------+---------+---------+ 180
CGTCGTTCACTGCTCTCTAGTAGGGTGAGCAAACCACTGCGACGTTTTATGTTCACATAA

ATACGGTCAGTCGGCTCTACAACATTCAAAACGAGTTGTCTCGCTTCAACCACAAAGCGC
---------+---------+---------+---------+---------+---------+ 240
TATGCCAGTCAGCCGAGATGTTGTAAGTTTTGCTCAACGAGCGAAGTTGGTGTTTCGCG

CACACT
------ 246
GTGTGA
```

TABLE 9

Nucleotide sequence of the cDNA and amino-acid sequence
derived therefrom of the *T. gondii* antigen P35

(SEQ ID NOS:15–16)
```
    CAGTTTCCGCGCTGTAGTAAGATGGCTTTACCATTGCGTGTTTCGGCCACGGTGTTCGTG
  1 ---------+---------+---------+---------+---------+---------+  60
    GTCAAAGGCGCGACATCATTCTACCGAAATGGTAACGCACAAAGCCGGTGCCACAAGCAC
                          MetAlaLeuProLeuArgValSerAlaThrValPheVal

GTCTTCGCTGTCTTTGGTGTAGCTCGCGCCATGAACGGTCCTTTTGAGTTATCATCCAAGC
 61 ---------+---------+---------+---------+---------+---------+ 120
    CAGAAGCGACAGAAACCACATCGAGCGCGGTACTTGCCAGGAAACTCAATAGTAGGTTCG
    ValPheAlaValPheGlyValAlaArgAlaMetAsnGlyProLeuSerTyrHisProSer

AGTTACGGAGCGTCGTATCCGAATCCGAGTAATCCTCTGCATGGAATGCCCAAGCCAGAG
121 ---------+---------+---------+---------+---------+---------+ 180
    TCAATGCCTCGCAGCATAGGCTTAGGCTCATTAGGAGACGTACCTTACGGTTCGGTCTC
    SerTyrGlyAlaSerTyrProAsnProSerAsnProLeuHisGlyMetProLysProGlu

AACCCGGTGAGACCGCCTCCTCCCGGTTTCCATCCAAGCGTTATTCCCAATCCCCCGTAC
181 ---------+---------+---------+---------+---------+---------+ 240
    TTGGGCCACTCTGGCGGAGGAGGGCCAAAGGTAGGTTCGCAATAAGGGTTAGGGGCATG
    AsnProValArgProProProGlyPheHisProSerValIleProAsnProProTyr

CCGCTGGGCACTCCAGCGAGCATGCCACAGCCAGAGGTTCCGCCACTTCAGCATCCCCCG
241 ---------+---------+---------+---------+---------+---------+ 300
    GGCGACCCGTGAGGTCGCTCGTACGGTGTCGGTCTCCAAGGCGGTGAAGTCGTAGGGGGC
    ProLeuGlyThrProAlaSerMetProGlnProGluValProProLeuGlnHisProPro

CCAACGGGTTCCCCTCCCGCGGCCCGTCCCCAGCCTCCATATCCAGTGGGTACTCCAGTA
301 ---------+---------+---------+---------+---------+---------+ 360
    GGTTGCCCAAGGGGAGGGCGCCGGCGAGGGGTCGGAGGTATAGGTCACCCATGAGGTCAT
    ProThrGlySerProProAlaAlaAlaProGlnProProTyrProValGlyThrProVal

ATGCCACAGCCAGAGATACCGCCTGTTCATCGGCCGCCGCCTCCGGGTTTCCGTCCCGAA
361 ---------+---------+---------+---------+---------+---------+ 420
    TACGGTGTCGGTCTCTATGGCGGACAAGTAGCCCGCGGCGGAGGCCCAAAGGCAGGGCTT
    MetProGlnProGluIleProProValHisArgProProProProGlyPheArgProGlu

GTGGCTCCCGTGCCCCCGTATCCAGTGGGCACTCCAACGGGCATGCCCCAGCCGGAGATA
421 ---------+---------+---------+---------+---------+---------+ 480
    CACCGAGGGCACGGGGCATAGGTCACCCGTGAGGTTGCCCGTACGGGGTCGGCCTCTAT
    ValAlaProValProProTyrProValGlyThrProThrGlyMetProGlnProGluIle

CCGGCAGTTCACCATCCGTTCCCCTACGTTACGACAACCACGACAGCTGCTCCTCGTGTG
481 ---------+---------+---------+---------+---------+---------+ 540
    GGCCGTCAAGTGGTAGGCAAGGGGATGCAATGCTGTTGGTGCTGTCGACGAGGAGCACAC
    ProAlaValHisHisProPheProTyrValThrThrThrThrAlaAlaProArgVal

CTGGTTTATAAGATTCCCTATGGAGGCGCTGCACCCCCCCGTGCTCCTCCAGTGCCACCC
541 ---------+---------+---------+---------+---------+---------+ 600
    GACCAAATATTCTAAGGGATACCTCCGCGACGTGGGGGGGCACGAGGAGGTCACGGTGGG
```

TABLE 9-continued

Nucleotide sequence of the cDNA and amino-acid sequence
derived therefrom of the *T. gondii* antigen P35

```
    LeuValTyrLysIleProTyrGlyGlyAlaAlaProProArgAlaProProValProPro

CGTATGGGCCCGAGTGATATCAGCACTCACGTGCGGGGTGCAATCCGGCGTCAACCCGGT
601 ---------+---------+---------+---------+---------+---------+ 660
    GCATACCCGGGCTCACTATAGTCGTGAGTGCACGCCCCACGTTAGGCCGCAGTTGGGCCA
    ArgMetGlyProSerAspIleSerThrHisValArgGlyAlaIleArgArgGlnProGly

ACCACCACCACCACTACTTCCCGCAAACTACTATTCAGGACAGCGGTAGTGGCTGCAATG
661 ---------+---------+---------+---------+---------+---------+ 720
    TGGTGGTGGTGGTGATGAAGGGCGTTTGATGATAAGTCCTGTCGCCATCACCGACGTTAC
    ThrThrThrThrThrThrSerArgLysLeuLeuPheArgThrAlaValValAlaAlaMet

GCAGCAGCCTTGATAACCCTGTTCAGACAAAGACCTGTGTTCATGGAGGGGACGGGATG
721 ---------+---------+---------+---------+---------+---------+ 780
    CGTCGTCGGAACTATTGGGACAAGTCTGTTTCTGGACACAAGTACCTCCCCCATGCCTAC
    AlaAlaAlaLeuIleThrLeuPheArgGlnArgProValPheMetGluGlyValArgMet

TTTCCAAATCTCCACTACAGATTCACCGTAACGACGCAGAATTAAATTTCCCGTTGACGA
781 ---------+---------+---------+---------+---------+---------+ 840
    AAAGGTTTAGAGGTGATGTCTAAGTGGCATTGCTGCGTCTTAATTTAAAGGCCAACTGCT
    PheProAsnLeuHisTyrArgPheThrValThrThrGlnAsn

ATATAGAAGTCACTTATACAGTGGGTACACGACCTTCGTGGCGTCCACACCTTGTTTCCG
841 ---------+---------+---------+---------+---------+---------+ 900
    TATATCTTCAGTGAATATGTCACCCATGTGCTGGAAGCACCGCAGGTGTGGAACAAAGGC

TTCCGGTCACAGGTTGTGTCTACAAACGAACACGGTGGTATGTGCTGTAGACTCAGGGGT
901 ---------+---------+---------+---------+---------+---------+ 960
    AAGGCCAGTGTCCAACACAGATGTTTGCTTGTGCCACCATACACGACATCTGAGTCCCCA

GGGAGGAGCGCTGTAGGGCCTTCTGGAGAGCTCTCAATGTGCGCTATCCGCTTATATTCG
961 ---------+---------+---------+---------+---------+---------+ 1020
    CCCTCCTCGCGACATCCCGGAAGACCTCTCGAGAGTTACACGCGATAGGCGAATATAAGC

TGCAGCGTTATCCTCGTGAGGAGCGTCGATTGTGTCGTGCCCAGTGTCGCCGGACTCGAA
1021 ---------+---------+---------+---------+---------+---------+ 1080
     ACGTCGCAATAGGAGCACTCCTCGCAGCTAACACAGCACGGGTCACAGCGGCCTGAGCTT

TCAGAAACCTGC
1081 ----------+-- 1092
     AGTCTTTGGACG
```

TABLE 10

Nucleotide sequence of the cDNA and amino-acid secquence
derived therefrom of the *T. gondii* antigen P66

(SEQ ID NOS:17—18)
```
    TTGCTGTCGCCGTTGCTGTCGCATATACTGCACTGACTTCGACACCATGGAGCAAAGGCT
  1 ---------+---------+---------+---------+---------+---------+ 60
    AACGACAGCGGCAACGACAGCGTATATGACGTGACTGAAGCTGTGGTACCTCGTTTCCGA
                                                       MetGluGlnArgLe

GCCAATTATTCTACTTGTTCTCTCTGTGTTCTTCAGTTCAACCCCAAGCGCCGCCCTTTC
 61 ---------+---------+---------+---------+---------+---------+ 120
    CGGTTAATAAGATGAACAAGAGAGACACAAGAAGTCAAGTTGGGGTTCGCGGCGGGAAAG
    uProIleIleLeuLeuValLeuSerValPhePheSerSerThrProSerAlaAlaLeuSe

GAGCCACAATGGAGTCCCCGCTTATCCATCGTATGCACAGGTATCGCTCTCTTCCAACGG
121 ---------+---------+---------+---------+---------+---------+ 180
    CTCGGTGTTACCTCAGGGGCGAATAGGTAGCATACGTGTCCATAGCGAGAGAAGGTTGCC
    rSerHisAsnGlyValProAlaTyrProSerTyrAlaGlnValSerLeuSerSerAsnGl

CGAGCCACGGCACAGGGGCATACGCGGCAGCTTCCTCATGTCCGTAAAGCCACACGCAAA
181 ---------+---------+---------+---------+---------+---------+ 240
    GCTCGGTGCCGTGTCCCCGTATGCGCCGTCGAAGGAGTACAGGCATTTCGGTGTGCGTTT
    yGluProArgHisArgGlyIleArgGlySerPheLeuMetSerValLysProHisAlaAs

CGCTGATGACTTCGCCTCCGACGACAACTACGAACCGCTGCCGAGTTTCGTGGAAGCTCC
241 ---------+---------+---------+---------+---------+---------+ 300
    GCGACTACTGAAGCGGAGGCTGCTGTTGATGCTTGGCGACGGCTCAAAGCACCTTCGAGG
    nAlaAspAspPheAlaSerAspAspAsnTyrGluProLeuProSerPheValGluAlaPr
```

TABLE 10-continued

Nucleotide sequence of the cDNA and amino-acid secquence derived therefrom of the T. gondii antigen P66

```
    TGTCAGAGGCCCGGACCAAGTCCCTGCCAGAGGAGAAGCTGCTCTTGTCACAGAGGAGAC
301 ---------+---------+---------+---------+---------+---------+ 360
    ACAGTCTCCGGGCCTGGTTCAGGGACGGTCTCCTCTTCGACGAGAACAGTGTCTCCTCTG
    oValArgGlyProAspGlnValProAlaArgGlyGluAlaAlaLeuValThrGluGluTh

TCCAGCGCAACAGCCGGCGGTGGCTCTAGGCAGTGCAGAAGGGGAGGGGACTCCACCTAC
361 ---------+---------+---------+---------+---------+---------+ 420
    AGGTCGCGTTGTCGGCCGCCACCGAGATCCGTCACGTCTTCCCCTCCCCTGAGGTGGATG
    rProAlaGlnGlnProAlaValAlaLeuGlySerAlaGluGlyGluGlyThrProProTh

TGAATCCGCCTCCGAAAATTCTGAAGATGATGACACGTTTCACGATGCCCTCCAAGAGCT
421 ---------+---------+---------+---------+---------+---------+ 480
    ACTTAGGCGGAGGCTTTTAAGACTTCTACTACTGTGCAAAGTGCTACGGGAGGTTCTCGA
    rGluSerAlaSerGluAsnSerGluAspAspAspThrPheHisAspAlaLeuGlnGluLe

TCCAGAGGATGGCCTCGAAGTGCGCCCACCAAATGCACAGGAGCTGCCCCCACCAAATGT
481 ---------+---------+---------+---------+---------+---------+ 540
    AGGTCTCCTACCGGAGCTTCACGCGGGTGGTTTACGTGTCCTCGACGGGGGTGGTTTACA
    uProGluAspGlyLeuGluValArgProProAsnAlaGlnGluLeuProProProAsnVa

ACAGGAGCTGCCCCCACCAAATGTACAGGAGCTGCCCCCACCAACTGAACAGGAGCTGCC
541 ---------+---------+---------+---------+---------+---------+ 600
    TGTCCTCGACGGGGGTGGTTTACATGTCCTCGACGGGGGTGGTTGACTTGTCCTCGACGG
    lGlnGluLeuProProProAsnValGlnGluLeuProProProThrGluGlnGluLeuPr

CCCACCAACTGAACAGGAGCTGCCCCCACCAACTGAACAGGAGCTGCCCCCACCAACTGA
601 ---------+---------+---------+---------+---------+---------+ 660
    GGGTGGTTGACTTGTCCTCGACGGGGGTGGTTGACTTGTCCTCGACGGGGGTGGTTGACT
    oProProThrGluGlnGluLeuProProProThrGluGlnGluLeuProProProThrGl

ACAGGAGCTAGCCCCATCAACTGAACAGGAGCTGCCCCCACCAGTGGGCGAAGGTCAACG
661 ---------+---------+---------+---------+---------+---------+ 720
    TGTCCTCGATCGGGGTAGTTGACTTGTCCTCGACGGGGGTGGTCACCCGCTTCCAGTTGC
    uGlnGluLeuAlaProSerThrGluGlnGluLeuProProProValGlyGluGlyGlnAr

TCTGCAAGTCCCTGGGGAACATGGGCCACAGGGGCCCCCATACGATGATCAGCAGCTGCT
721 ---------+---------+---------+---------+---------+---------+ 780
    AGACGTTCAGGGACCCCTTGTACCCGGTGTCCCCGGGGGTATGCTACTAGTCGTCGACGA
    gLeuGlnValProGlyGluHisGlyProGlnGlyProProTyrAspAspGlnGlnLeuLe

TTTAGAGCCTACGGAAGAGCAACAGGAGGGCCCTCAGGAGCCGCTGCCACCGCCGCCGCC
781 ---------+---------+---------+---------+---------+---------+ 840
    AAATCTCGGATGCCTTCTCGTTGTCCTCCCGGGAGTCCTCGGCGACGGTGGCGGCGGCGG
    uLeuGluProThrGluGluGlnGlnGluGlyProGlnGluProLeuProProProProPr

CCCGACTCGGGGCGAACAACCCGAAGGACAGCAGCCGCAGGGACCAGTTCGTCAAAATTT
841 ---------+---------+---------+---------+---------+---------+ 900
    GGGCTGAGCCCCGCTTGTTGGGCTTCCTGTCGTCGGCGTCCCTGGTCAAGCAGTTTTAAA
    oProThrArgGlyGluGlnProGluGlyGlnGlnProGlnGlyProValArgGlnAsnPh

TTTTCGTCGGGCGTTGGGGGCCGCAAGAAGCCGATTCGGAGGTGCACGACGCCATGTCAG
901 ---------+---------+---------+---------+---------+---------+ 960
    AAAAGCAGCCCGCAACCCCCGGCGTTCTTCGGCTAAGCCTCCACGTGCTGCGGTACAGTC
    ePheArgArgAlaLeuGlyAlaAlaArgSerArgPheGlyGlyAlaArgArgHisValSe

TGGGGTGTTCCGAAGAGTCAGAGGTGGTTTGAACCGTATAGTAGGTGGAGTGAGGAGTGG
961 ---------+---------+---------+---------+---------+---------+ 1020
    ACCCCACAAGGCTTCTCAGTCTCCACCAAACTTGGCATATCATCCACCTCACTCCTCACC
    rGlyValPheArgArgValArgGlyGlyLeuAsnArgIleValGlyGlyValArgSerGl

TtTCAGGCGTGCAAGAGAAGGTGTCGTTGGGGGAGTCCGTCGTTTAACAAGTGGTGCCAG
1021 ---------+---------+---------+---------+---------+---------+ 1080
    AAAGTCCGCACGTTCTCTTCCACAGCAACCCCCTCAGGCAGCAAATTGTTCACCACGGTC
    yPheArgArgAlaArgGluGlyValValGlyGlyValArgArgLeuThrSerGlyAlaSe

TCTGGGTCTCGGTCGTGTAGGAGAAGGTTTAGGTAGGAGTTTCTATCGTGTAAGAGGAGC
1081 ---------+---------+---------+---------+---------+---------+ 1140
    AGACCCAGAGCCAGCACATCCTCTTCCAAATCCATCCTCAAAGATAGCACATTCTCCTCG
    rleuGlyLeuGlyArgValGlyGluGlyLeuGlyArgSerPheTyrArgValArgGlyAl TGTCAGTAGCGGTCGTAGGCGTGCAGCAGATGGTGCCAGCAATGTAAGAGAAAGATTCGT
1141 ---------+---------+---------+---------+---------+---------+ 1200
    ACAGTCATCGCCAGCATCCGCACGTCGTCTACCACGGTCGTTACATTCTCTTTCTAAGCA
    aValSerSerGlyArgArgArgAlaAlaAspGlyAlaSerAsnValArgGluArgPheVa

TGCCGCAGGCGGGAGAGTCAGAGACGCTTTCGGCGCGGGATTGACGCGCCTCCGCAGGCG
```

TABLE 10-continued

Nucleotide sequence of the cDNA and amino-acid secquence derived therefrom of the *T. gondii* antigen P66

```
     ACGGCGTCCGCCCTCTCAGTCTCTGCGAAAGCCGCGCCCTAACTGCGGGGAGGCGTCCGC
1201 ---------+---------+---------+---------+---------+---------+ 1260
     TGCCGCAGGCGGGAGAGTCAGAGACGCTTTCGGCGCGGGATTGACGCCCCTCCGCAGGCG
      lAlaAlaGlyGlyArgValArgAspAlaPheGlyAlaGlyLeuThrArgLeuArgArgAr

CGGCAGAACTAATGGCGAGGAGGGCAGGCCCCTACTGGGCGAAGGAAGAGAGCAGGATGA
1261 ---------+---------+---------+---------+---------+---------+ 1320
     GCCGTCTTGATTACCGCTCCTCCCGTCCGGGGATGACCCGCTTCCTTCTCTCGTCCTACT
      gGlyArgThrAsnGlyGluGluGlyArgProLeuLeuGlyGluGlyArgGluGlnAspAs

TGGATCGCAATAATACGGGCAGCATGCTGCTGGATTCGGCGAAGACGACCGTTTCTCGTA
1321 ---------+---------+---------+---------+---------+---------+ 1360
     ACCTAGCGTTATTATGCCCGTCGTACGACGACCTAAGCCGCTTCTGCTGGCAAAGAGCAT
      pGlySerGln

AACGACAGCGGGTCCTCCGAAGTTAAGAAACCCGGTAAACGTGTGTGCCGTAACGGTGAT
1381 ---------+---------+---------+---------+---------+---------+ 1440
     TTGCTGTCGCCCAGGAGGCTTCAATTCTTTGGGCCATTTGCACACACGGCATTGCCACTA

CGAGTTTGCAGATGGTTCCTTGTGTACCACGTGGCTTCTCGAGACCAATCGTGCTTTGTT
1441 ---------+---------+---------+---------+---------+---------+ 1500
     GCTCAAACGTCTACCAAGGAACACATGGTGCACCGAAGAGCTCTGGTTAGCACGAAACAA

AGGGTCTAGTAGTTCGGACAGGATTTTATTGAACTGCAGGAATGCTTGCAGAAGAGAAGC
1501 ---------+---------+---------+---------+---------+---------+ 1560
     TCCCAGATCATCAAGCCTGTCCTAAAATAACTTGACGTCCTTACGAACGTCTTCTCTTCG

CGTGAGGCAATGCAGGTTCTTGCGTCTGTGCGAGCAGGACTTGAAAGATTCGTTGTGGTG
1561 ---------+---------+---------+---------+---------+---------+ 1620
     GCACTCCGTTACGTCCAAGAACGCAGACACGCTCGTCCTGAACTTTCTAAGCAACACCAC

GCAACCTTGTGCCTATCTATCCGAAGCCTCGCTGACTCGCAGAAATAAGGGTCGAGATCC
1621 ---------+---------+---------+---------+---------+---------+ 1680
     CGTTGGAACACGGATAGATAGGCTTCGGAGCGACTGAGCGTCTTTATTCCCAGCTCTAGG

ATGAGAGCTTTCTGGGTGGTGAGGCCAGGGCTTGTGAGAACTTCGTGGGAAGATGTGCTT
1681 ---------+---------+---------+---------+---------+---------+ 1740
     TACTCTCGAAAGACCCACCACTCCGGTCCCGAACACTCTTGAAGCACCCTTCTACACGAA

GAGCTTCGTCAGCAACTTCACGGAGAGCGCCACCTGATCTAAACATCCGAACATTTTTAG
1741 ---------+---------+---------+---------+---------+---------+ 1800
     CTCGAAGCAGTCGTTGAAGTGCCTCTCGCGGTGGACTAGATTTGTAGGCTTGTAAAAATC

CTCGACATGTTCACAGAAATGTTGATAGGTTGAGGCGTGTAAAGGTTCGTTCTGGGAAGA
1801 ---------+---------+---------+---------+---------+---------+ 1860
     GAGCTGTACAAGTGTCTTTACAACTATCCAACTCCGCACATTTCCAAGCAAGACCCTTCT

CGAGTAATCATGTCACGCCATGTTAGCGGTCATGTCGCTGCCTCATTGTATTCGGGTGTC
1861 ---------+---------+---------+---------+---------+---------+ 1920
     GCTCATTAGTACAGTGCGGTACAATCGCCAGTACAGCGACGGAGTAACATAAGCCCACAG

ACTGTGCCTTCAAACATCAGTCGTGGTTCAGCAGTGTTTGCTGACGTTCGACACACGGAA
1921 ---------+---------+---------+---------+---------+---------+ 1980
     TGACACGGAAGTTTGTAGTCAGCACCAAGTCGTCACAAACGACTGCAAGCTGTGTGCCTT

CTCCGGCGAGACTGTCTCGGCAAATGTGACGCACTTTGTATTCATGIGGCAAACCGTTTC
1981 ---------+---------+---------+---------+---------+---------+ 2040
     GAGGCCGCTCTGACAGAGCCGTTTACACTGCGTGAAACATAAGTACACCGTTTGGCAAAG

AACGCGGTAATGTGTTTCTTGTTAAAAAAAAAA
2041 ---------+---------+---------+---- 2074
     TTGCGCCATTACACAAAAGAACAATTTTTTTTT
```

TABLE 11

Nucleotide sequence of the cDNA and amino-acid sequence derived therefrom of the *T. gondii* antigen P68

(SEQ ID NOS:19—20)

```
   GCCACTGCTGTGTCTGAAGCGTGCCGATGTGTGCGCGTACGCTTACAGAGAGCCTGCAAG
 1 ---------+---------+---------+---------+---------+---------+ 60
   CGGTGACGACACAGACTTCGCACGGCTACACACGCGCATGCGAATGTCTCTCGGACGTTC

ACACTGCTTGGAAGACAAAATTTTTCTTCTCAAGAGTTGAGCTTTAGTTTGGTCACTCGC
```

TABLE 11-continued

Nucleotide sequence of the cDNA and amino-acid sequence
derived therefrom of the *T. gondii* antigen P68

```
 61 ---------+---------+---------+---------+---------+---------+ 120
    TGTGACCAACCTTCTGTTTTAAAAAGAAGAGTTCTCAACTCGAAATCAAACCAGTGAGCG

CGTTGGTTGTTCTGTGTGCTAGACGTACTCTAACGCAAACCAGTCGAGGAACACACGAAC
121 ---------+---------+---------+---------+---------+---------+ 180
    GCAACCAACAAGACACACGATCTGCATGAGATTGCGTTTGGTCAGCTCCTTGTGTGCTTG

GAGAGAGACGGCAATATCTCCCGTCGCGCTATCATACCGGCAACATGGATTGCGGACAGT
181 ---------+---------+---------+---------+---------+---------+ 240
    CTCTCTCTGCCGTTATAGAGGGCAGCGCGATAGTATGGCCGTTGTACCTAACGCCTGTCA
                                                    MetAspCysGlyGlnC

GCAGAAGGCAACTGCACGCAGCAGGTGTTCTAGGCTTGTTTGTCACCCTTGCCACAGCAA
241 ---------+---------+---------+---------+---------+---------+ 300
    CGTCTTCCGTTGACGTGCGTCGTCCAGAAGATCCGAACAAACAGTGGGAACGGTGTCGTT
    ysArgArgGlnLeuHisAlaAlaGlyValLeuGlyLeuPheValThrLeuAlaThrAlaT

CCGTAGGATTGAGCCAAAGGGTGCCAGAGCTACCAGAAGTGGAGTCCTTTGATGAAGTAG
301 ---------+---------+---------+---------+---------+---------+ 360
    GGCATCCTAACTCGGTTTCCCACGGTCTCGATGGTCTTCACCTCAGGAAACTACTTCATC
    hrValGlyLeuSerGlnArgValProGluLeuProGluValGluSerPheAspGluValG

GCACGGGAGCTCGACGGTCCGGGTCCATTGCGACCCTTCTTCCACAAGACGTCTGTTTTAT
361 ---------+---------+---------+---------+---------+---------+ 420
    CGTGCCCTCGAGCTGCCAGGCCCAGGTAACGCTGGGAAGAAGGTGTTCTGCGACAAAATA
    lyThrGlyAlaArgArgSerGlySerIleAlaThrLeuLeuProGlnAspAlaValLeuT

ATGAGAACTCAGAGGACGTTGCCGTTCCGAGTGATTCAGCATCGACCCCGTCATACTTTC
421 ---------+---------+---------+---------+---------+---------+ 480
    TACTCTTGAGTCTCCTGCAACGGCAAGGCTCACTAAGTCGTAGCTGGGGCAGTATGAAAG
    yrGluAsnSerGluAspValAlaValProSerAspSerAlaSerThrProSerTyrPheH

ATGTGGAATCTCCAAGTGCTAGTGTGGAAGCCGCGACTGGCGCGGTGGGAGAGGTGGTGC
481 ---------+---------+---------+---------+---------+---------+ 540
    TACACCTTAGAGGTTCACGATCACACCTTCGGCGCTGACCGCGCCACCCTCTCCACCACG
    isValGluSerProSerAlaSerValGluAlaAlaThrGlyAlaValGlyGluValValP

CGGACTGTGAAGAACGACAGGAACAGGGTGACACGACGTTATCCGATCACGATTTCCATT
541 ---------+---------+---------+---------+---------+---------+ 600
    GCCTGACACTTCTTGCTGTCCTTGTCCCACTGTGCTGCAATAGGCTAGTGCTAAAGGTAA
    roAspCysGluGluArgGlnGluGlnGlyAspThrThrLeuSerAspHisAspPheHisS

CAGGTGGAACTGAACAGGAGGGTTTGCCGGAAACAGAGGTGGCGCATCAGCATGAGACAG
601 ---------+---------+---------+---------+---------+---------+ 660
    GTCCACCTTGACTTGTCCTCCCAAACGGCCTTTGTCTCCACCGCGTAGTCGTACTCTGTC
    erGlyGlyThrGluGlnGluGlyLeuProGluThrGluValAlaHisGlnHisGluThrG

AAGAACAGTACGGGACTGAAGGGATGCCCCCCCCTGTTCTGCCACCTGCACCGGTAGTCC
661 ---------+---------+---------+---------+---------+---------+ 720
    TTCTTGTCATGCCCTGACTTCCCTACGGGGGGGACAAGACGGTGGACGTGGCCATCAGG
    luGluGlnTyrGlyThrGluGlyMetProProProValLeuProProAlaProValValH

ATCCGCGTTTTATTGCAGTACCAGGGCCGTCGGTGCCTGTTCCATTTTTCAGTTTGCCAG
721 ---------+---------+---------+---------+---------+---------+ 780
    TAGGCGCAAAATAACGTCATGGTCCCGGCAGCCACGGACAAGGTAAAAAGTCAAACGGTC
    isProArgPheIleAlaValProGlyProSerValProValProPhePheSerLeuProA

ACATCCACCCGGATCAGGTTGTGTATATTCTAAGGGTTCAGGGATCTGGGGACTTCGACA
781 ---------+---------+---------+---------+---------+---------+ 840
    TGTAGGTGGGCCTAGTCCAACACATATAAGATTCCCAAGTCCCTAGACCCCTGAAGCTGT
    spIleHisProAspGlnValValTyrIleLeuArgValGlnGlySerGlyAspPheAspI

TCAGTTTCGAAGTTGGCCGAGCTGTGAAGCAGTTGGAAGCCATCAAGAAAGCATACAGAG
841 ---------+---------+---------+---------+---------+---------+ 900
    AGTCAAAGCTTCAACCGGCTCGACACTTCGTCAACCTTCGGTAGTTCTTTCGTATGTCTC
    leSerPheGluValGlyArgAlaValLysGlnLeuGluAlaIleLysLysAlaTyrArgG

AAGCCACCGGGAAGCTAGAAGCAGACGAGCTTGAGTCAGAAAGGGGACCTGCTGTTTCAC
901 ---------+---------+---------+---------+---------+---------+ 960
    TTCGGTGGCCCTTCGATCTTCGTCTGCTCGAACTCAGTCTTTCCCCTGGACGACAAAGTG
    luAlaThrGlyLysLeuGluAlaAspGluLeuGluSerGlnArgGlyProAlaValSerP

CTCGACGAAGGCTGGTTGACCTGATCAAAGATAACCAGCGACGACTCAGGGCGGCGCTTC
961 ---------+---------+---------+---------+---------+---------+ 1020
    GAGCTGCTTCCGACCAACTGGACTAGTTTCTATTGGTCGCTGCTGAGTCCCGCCGCGAAG
    roArgArgArgLeuValAspLeuIleLysAspAsnGlnArgArgLeuArgAlaAlaLeuG
```

TABLE 11-continued

Nucleotide sequence of the cDNA and amino-acid sequence
derived therefrom of the *T. gondii* antigen P68

```
     AGAAGATAAAGATACAGAAAAAGTTGGAGGAGATTGATGACTTACTTCAGCTGACACGCG
1021 ---------+---------+---------+---------+---------+---------+ 1080
     TCTTCTATTTCTATGTCTTTTTCAACCTCCTCTAACTACTGAATGAAGTCGACTGTCGC
     lnLysIleLysIleGlnLysLysLeuGluGluIleAspAspLeuLeuGlnLeuThrArgA

CACTGAAGGCCATGGATGCCCGTCTGAGAGCCTGCCAGGATATGGCACCGATTGAGGAG
1081 ---------+---------+---------+---------+---------+---------+ 1140
     GTGACTTCCGGTACCTACGGGCAGACTCTCGGACGGTCCTATACCGTGGCTAACTCCTCC
     laLeuLysAlaMetAspAlaArgLeuArgAlaCysGlnAspMetAlaProIleGluGluA

CGCTGTGTCACAAGACGAAGGCGTTTGGAGAAATGGTGTCCCAGAAAGCCAAGGAAATTC
1141 ---------+---------+---------+---------+---------+---------+ 1200
     GCGACACAGTGTTCTGCTTCCGCAAACCTCTTTACCACAGGGTCTTTCGGTTCCTTTAAG
     laLeuCysHisLysThrLysAlaPheGlyGluMetValSerGlnLysAlaLysGluIleA

GGGAGAAAGCGGCGTCCTTGTCTTCATTGTTAGGTGTCGATGCTGTCGAAAAAGAATTGC
1201 ---------+---------+---------+---------+---------+---------+ 1260
     CCCTCTTTCGCCGCAGGAACAGAAGTAACAATCCACAGCTACGACAGCTTTTTCTTAACG
     rgGluLysAlaAlaSerLeuSerSerleuLeuGlyValAspAlaValGluLysGluLeuA GGCGTGTCGAACCGGAACATGAAGATAACACCAGAGTTGAAGCCAGGGTAGAGGAATTGC
1261 ---------+---------+---------+---------+---------+---------+ 1320
     CCGCACAGCTTGGCCTTGTACTTCTATTGTGGTCTCAACTTCGGTCCCATCTCCTTAACG
     rgArgValGluProGluHisGluAspAsnThrArgValGluAlaArgValGluGluLeuG AGAAGGCGCTGGAGAAGGCCGCGTCTGAGGCAAAGCAGCTCGTGGGGACCGCAGCAGGGC
1321 ---------+---------+---------+---------+---------+---------+ 1380
     TCTTCCGCGACCTCTTCCGGCGCAGACTCCGTTTCGTCGAGCACCCCTGGCGTCGTCCGC
     lnLysAlaLeuGluLysAlaAlaSerGluAlaLysGlnLeuValGlyThrAlaAlaGlyG AAATAGAGGAAGGAGTAAAAGCGGATACTCAGGCTGTGCAAGATAGCTCGAAAGACGTGT
1381 ---------+---------+---------+---------+---------+---------+ 1440
     TTTATCTCCTTCCTCATTTTCGCCTATGAGTCCGACACGTTCTATCGAGCTTTCTGCACA
     luIleGluGluGlyValLysAlaAspThrGlnAlaValGlnAspSerSerLysAspValL TGACGAAGAGTCCAGTTGCGCTCGTGGAAGCCTTTAAAGCGATCCAGAGGGCTCTTCTTG
1441 ---------+---------+---------+---------+---------+---------+ 1500
     ACTGCTTCTCAGGTCAACGCGAGCACCTTCGGAAATTTCGCTAGGTCTCCCGAGAAGAAC
     euThrLysSerProValAlaLeuValGluAlaPheLysAlaIleGlnArgAlaLeuLeuG AGGCGAAGACAAAGGAACTAGTAGAGCCTACGTCTAAAGAAGCGGAGGAAGCTCGTGAGA
1501 ---------+---------+---------+---------+---------+---------+ 1560
     TCCGCTTCTGTTTCCTTGATCATCTCGGATGCAGATTTCTTCGCCTCCTTCGAGCAGTCT
     luAlaLysThrLysGluLeuValGluProThrSerLysGluAlaGluGluAlaArgGlnI TCTTAGCGGAACAGGCAGCTTGATTTCCCAAGGATGCAGTTAAAGATGGGGATGCATGAT
1561 ---------+---------+---------+---------+---------+---------+ 1620
     AGAATCGCCTTGTCCGTCGAACTAAAGGGTTCCTACGTCAATTTCTACCCCTACGTACTA
     leLeuAlaGluGlnAlaAla AGGTAGCGCGCCCATTATCCCAATCCTTTAGCCGTCTACCGTGACGTGGATCATTATAGG
1621 ---------+---------+---------+---------+---------+---------+ 1680
     TCCATCGCGCGGGTAATAGGGTTAGGAAATCGGGAGATGGCACTGCACCTAGTAATATCC GGAAACAAGCATTAGCAGAATGATCGTGTATCGCGGAACACACGCATATCCGCACCAGTT
1681 ---------+---------+---------+---------+---------+---------+ 1740
     CCTTTGTTCGTAATCGTCTTACTAGCACATAGCGCCTTGTGTGCGTATAGGCGTGGTCAA TTTCTAACGTATGGTGAATGGGTTCAAGTCTGGGTTCAAGGCGCAGTGTCTATGCAACAG
1741 ---------+---------+---------+---------+---------+---------+ 1800
     AAAGATTGCATACGACTTACCCAAGTTCAGACCCAAGTTCCGCGTCACAGATACGTTGTC CGCCGGTTTCTGCCCTTCGTTTTTGCACATGTGCACAGGTATGTACAGTGTTTATGTATA
1801 ---------+---------+---------+---------+---------+---------+ 1860
     GCGGCCAAAGACGGGAAGCAAAAACGTGTACACGTGTCCATACATGTCACAAATACATAT TGGGGCAGTGTGCGCTTCGTCAATGATGTACAGAAAAAAAAAAAAAAAA
1861 ---------+---------+---------+-------------------  1909
     ACCCCGTCACACGCGAAGCAGTTACTACATGTCTTTTTTTTTTTTTTTT
```

TABLE 12

| | Western blot - Evaluation | | | |
|---|---|---|---|---|
| T. gondii protein | r-P29 | r-P35 | r-P66 | r-P68 |
| Expression plasmid | pPS29 | pPS76 | pPS61 | pPS34 |
| IgG | 5/16 | 25/26 | 21/31 | 27/31 |
| IgM | 0/21 | 2/21 | 17/21 | 0/21 |

TABLE 13

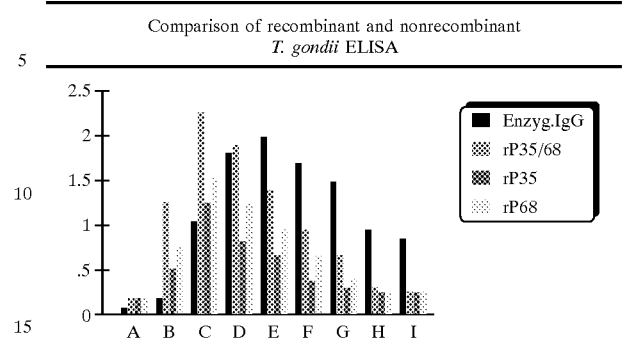

Comparison of recombinant and nonrecombinant *T. gondii* ELISA

What is claimed is:

1. A diagnostic which contains a monoclonal antibody or polyclonal antibody which specifically binds a substantially purified protein comprising at least one amino acid sequence selected from SEQ ID NOS: 2, 4, 6, 8, 10, 12, 16, 18, or 20, and immunogenic fragments thereof.

2. The diagnostic of claim 1, wherein the monoclonal antibody or polyclonal antibody specifically binds a substantially purified protein comprising SEQ ID NO:2.

3. The diagnostic of claim 1, wherein the monoclonal antibody or polyclonal antibody specifically binds a substantially purified protein comprising SEQ ID NO:4.

4. The diagnostic of claim 1, wherein the monoclonal antibody or polyclonal antibody specifically binds a substantially purified protein comprising SEQ ID NO:6.

5. The diagnostic of claim 1, wherein the monoclonal antibody or polyclonal antibody specifically binds a substantially purified protein comprising SEQ ID NO:8.

6. The diagnostic of claim 1, wherein the monoclonal antibody or polyclonal antibody specifically binds a substantially purified protein comprising SEQ ID NO:10.

7. The diagnostic of claim 1, wherein the monoclonal antibody or polyclonal antibody specifically binds a substantially purified protein comprising SEQ ID NO:12.

8. The diagnostic of claim 1, wherein the monoclonal antibody or polyclonal antibody specifically binds a substantially purified protein comprising SEQ ID NO:16.

9. The diagnostic of claim 1, wherein the monoclonal antibody or polyclonal antibody specifically binds a substantially purified protein comprising SEQ ID NO:18.

10. The diagnostic of claim 1, wherein the monoclonal antibody or polyclonal antibody specifically binds a substantially purified protein comprising SEQ ID NO:20.

11. A diagnostic which contains a monoclonal antibody or polyclonal antibody which specifically binds a substantially purified protein comprising an amino acid sequence encoded by a DNA sequence of SEQ ID NOS: 1, 3, 5, 7, 9, 11, 13, 14, 15, 17, or 19.

12. The diagnostic of claim 11, wherein the monoclonal antibody or polyclonal antibody specifically binds a substantially purified protein comprising an amino acid sequence encoded by a DNA sequence of SEQ ID NO: 1.

13. The diagnostic of claim 11, wherein the monoclonal antibody or polyclonal antibody specifically binds a substantially purified protein comprising an amino acid sequence encoded by a DNA sequence of SEQ ID NO: 3.

14. The diagnostic of claim 11, wherein the monoclonal antibody or polyclonal antibody specifically binds a substantially purified protein comprising an amino acid sequence encoded by a DNA sequence of SEQ ID NO: 5.

15. The diagnostic of claim 11, wherein the monoclonal antibody or polyclonal antibody specifically binds a substantially purified protein comprising an amino acid sequence encoded by a DNA sequence of SEQ ID NO: 7.

16. The diagnostic of claim 11, wherein the monoclonal antibody or polyclonal antibody specifically binds a substantially purified protein comprising an amino acid sequence encoded by a DNA sequence of SEQ ID NO: 9.

17. The diagnostic of claim 11, wherein the monoclonal antibody or polyclonal antibody specifically binds a substantially purified protein comprising an amino acid sequence encoded by a DNA sequence of SEQ ID NO: 11.

18. The diagnostic of claim 11, wherein the monoclonal antibody or polyclonal antibody specifically binds a substantially purified protein comprising an amino acid sequence encoded by a DNA sequence of SEQ ID NO: 13.

19. The diagnostic of claim 11, wherein the monoclonal antibody or polyclonal antibody specifically binds a substantially purified protein comprising an amino acid sequence encoded by a DNA sequence of SEQ ID NO: 14.

20. The diagnostic of claim 11, wherein the monoclonal antibody or polyclonal antibody specifically binds a substantially purified protein comprising an amino acid sequence encoded by a DNA sequence of SEQ ID NO: 15.

21. The diagnostic of claim 11, wherein the monoclonal antibody or polyclonal antibody specifically binds a substantially purified protein comprising an amino acid sequence encoded by a DNA sequence of SEQ ID NO: 17.

22. The diagnostic of claim 11, wherein the monoclonal antibody or polyclonal antibody specifically binds a substantially purified protein comprising an amino acid sequence encoded by a DNA sequence of SEQ ID NO: 19.

* * * * *